US008529951B1

(12) United States Patent
Ramamurthi et al.

(10) Patent No.: US 8,529,951 B1
(45) Date of Patent: Sep. 10, 2013

(54) ELASTOGENIC CUES AND METHODS FOR USING SAME

(76) Inventors: Anand Ramamurthi, Charleston, SC (US); Chandrasekhar Kothapalli, Tarrytown, NY (US); Binata Joddar, Dublin, OH (US)

( * ) Notice: Subject to any disclaimer, the term of this patent is extended or adjusted under 35 U.S.C. 154(b) by 382 days.

(21) Appl. No.: 12/034,237

(22) Filed: Feb. 20, 2008

Related U.S. Application Data

(60) Provisional application No. 60/890,934, filed on Feb. 21, 2007.

(51) Int. Cl.
*A61K 38/18* (2006.01)

(52) U.S. Cl.
USPC ............ 424/488; 424/461; 424/493; 514/7.6; 514/54; 514/499

(58) Field of Classification Search
USPC .................. 514/7.6, 54, 499; 424/461, 488, 424/493
See application file for complete search history.

(56) References Cited

U.S. PATENT DOCUMENTS

| | | | |
|---|---|---|---|
| 4,582,865 A | 4/1986 | Balazs et al. | |
| 4,965,353 A | 10/1990 | Della Valle et al. | |
| 5,079,236 A | 1/1992 | Drizen et al. | |
| 5,137,875 A | 8/1992 | Tsunenaga et al. | |
| 5,211,658 A * | 5/1993 | Clouse .................... | 623/1.14 |
| 5,646,129 A | 7/1997 | Callegaro et al. | |
| 5,667,800 A * | 9/1997 | De Vringer ............... | 424/450 |
| 6,232,303 B1 | 5/2001 | Callegaro et al. | |
| 6,391,861 B1 | 5/2002 | Cantor | |
| 6,645,945 B1 | 11/2003 | Radomsky et al. | |
| 6,846,906 B1 | 1/2005 | McCartney et al. | |
| 6,852,708 B2 | 2/2005 | Falk et al. | |
| 6,875,753 B1 | 4/2005 | Pilarski | |
| 6,929,626 B2 | 8/2005 | DiCarlo et al. | |
| 6,979,347 B1 | 12/2005 | Wu et al. | |
| 7,799,767 B2 | 9/2010 | Lamberti et al. | |
| 2001/0041180 A1 | 11/2001 | Staats et al. | |
| 2002/0106793 A1* | 8/2002 | West et al. ................ | 435/366 |
| 2002/0192205 A1 | 12/2002 | Michon et al. | |
| 2003/0032621 A1 | 2/2003 | Smadja-Joffe et al. | |
| 2003/0228364 A1 | 12/2003 | Nathan | |
| 2004/0162232 A1* | 8/2004 | Mitts et al. ................ | 514/2 |
| 2004/0265268 A1 | 12/2004 | Jain | |
| 2005/0079202 A1 | 4/2005 | Chen et al. | |
| 2005/0149175 A1* | 7/2005 | Hunter et al. ............. | 623/1.42 |
| 2005/0208114 A1 | 9/2005 | Petito et al. | |
| 2005/0208150 A1 | 9/2005 | Mitts et al. | |
| 2007/0224150 A1* | 9/2007 | Chung .................... | 424/70.14 |

FOREIGN PATENT DOCUMENTS

| | | | |
|---|---|---|---|
| CA | 1264671 A | * | 1/1990 |
| EP | 0295092 A2 | | 6/1988 |
| WO | WO 2006087392 A2 | * | 8/2006 |

OTHER PUBLICATIONS

Jain et al. 2005. Iron Oxide Nanoparticles for Sustained Delivery of Anticancer Agents. Molecular Pharmaceutics. vol. 2, No. 3, 194-205.*
Leroux et al. 1996. Biodegradable nanoparticles From sustained release formulations to improved site specific drug delivery. J. Controlled Release. vol. 39:339-350.*
Lavik et al. 2004. Tissue engineering: current state and perspectives. Appl. Microbiol. Biotechnol. 65: 1-8.*
Westedt et al. Deposition of Nanoparticles in the Arterial Vessel by Porous Balloon Catheters: Localization by Confocal Laser Scanning Microscopy and Transmission Electron Microscopy. AAPS PharmSci 2002; 4 (4) article 41 (http://www.aapspharmsci.org). p. 1-6.*
Gacheru et al. Structural and Catalytic Properties of Copper in Lysyl Oxidase. The Journal of Biological Chemistry. vol. 265, No. 31, Issue of Nov. 5, pp. 19022-19027,1990.*
Sinha et al. Synthesis of Nanosized Copper Powder by an Aqueous Route. Journal of Materials Synthesis and Processing, vol. 7, No. 6, 1999. p. 373-377.*
Amarnath, et al.; In Vitro Hemocomopatibility Testing of UV-modified Hyaluronan Hydrogels; pp. 1416-1424; 2006; Biomaterials; available online Sep. 6, 2005.
Joddar, et al.; Fragment Size and Dose-Specific Effects of Hyaluronan on Matrix Synthesis by Vascular Smooth Muscle Cells; pp. 2994-3004; Biomaterials; Available online Feb. 2, 2006.
Joddar, et al.; Elastogenic Effects of Exogenous Hyaluronan Oligosaccharides on Vascular Smooth Muscle Cells; pp. 5698-5707; Biomaterials; Available online Aug. 8, 2006.
Ramamurthi, et al.; Evaluation of the Matrix-Synthesis Potential of Crosslinked Hyaluronan Gels for Tissue Engineering of Aortic Heart Valves; pp. 999-1010; Biomaterials; Available online Jun. 7, 2004.
Joddar, et al.; Impact of Delivery Mode of Hyaluronan Oligomers on Elastogenic Responses of Adult Vascular Smooth Muscle Cells; pp. 3918-3927; Biomaterials; Available online Jun. 14, 2007.
Ibrahim, et al.; A Surface-Tethered Model to Assess Size-Specific Effects of Hyaluronan (HA) on Endothelial Cells; pp. 825-835; Biomaterials; Available online Oct. 11, 2006.
Ramamurthi, et al.; Ultraviolet light-induced Modification of Crosslinked Hyaluronan Gels; pp. 317-329; Sep. 23, 2002; Journal of Biomedical Materials Research Part A.
Kothapalli et al.; "Copper Nanoparticle Cues for Biomimetic Cellular Assembly of Crosslinked Elastin Fibers"; ActaBiomteriala, 5 (2009); pp. 541-553.

(Continued)

*Primary Examiner* — Taeyoon Kim
(74) *Attorney, Agent, or Firm* — Dority & Manning, PA

(57) ABSTRACT

Disclosed are elastogenic cues that can be utilized to encourage growth and development of elastin-containing cellular constructs. The elastogenic cues include hyaluronan fragments and oligomers, optionally in conjunction with growth factors and/or a source of copper ions. The elastogenic cues can up-regulate elastin matrix synthesis and by vascular smooth muscle cells. In addition to encouraging synthesis of elastin in a cellular matrix and organization into elastic fibers, the elastogenic cues can also stabilize the formed ECM matrix through suppression of elastin-laminin receptor (ELR). In addition, the elastogenic cues can inhibit cell hyper-proliferation (e.g., hyperplasia) common in inflammatory vascular disease.

22 Claims, 28 Drawing Sheets

(56) References Cited

OTHER PUBLICATIONS

Kothapalli et al.; "Biomimetic Regeneration of Elastin Matrices Using Hyaluronan and Copper Ion Cues"; Tissue Engineering: Part A; vol. 15, No. 1, 2009 pp. 103-113.

Gacchina, et al.; "Elastogenic Inductability of Smooth Muscle Cells from a Rat Model of Late State Abdominal Aortic Aneurysms"; Tissue Engineering: Part A; vol. 17, Nos. 13 and 14, 2011 pp. 1699-1711.

Gacchina, et al.; "Evaluating Smooth Muscle Cells From $CaCl_2$-Induced rat Aortal Expansions as a Surrogate culture Model for Study of Elastogenic Induction of Human Aneruysmal Cells"; Tissue Engineering: Part A; vol. 17, Nos. 16 and 17, 2011 pp. 1945-1957.

Kothapalli et al.; "Transforming Growth Factor Beta 1and Hyaluronan Oligomers Synergistically Enhance Elastin Matrix Regeneration by Vascular Smooth Muscle Cells"; Tissue Engineering: Part A; vol. 15, No. 3, 2009 pp. 501-511.

* cited by examiner

| HA Size (Daltons) | Dosage (mg/ml) | Tropoelastin | | Matrix Elastin (Soluble and Insoluble Fraction) | |
|---|---|---|---|---|---|
| | | Fastin Assay (10⁴ ng/ng DNA) relative to control | Band Intensity relative to control | Fastin Assay (10⁴ ng/ng DNA) relative to control | Desmosine relative to control (ng/ng) |
| Control | 0 | 1.0 ± 0.14 | 1.00 ± 0.04 | 1 ± 0.17 | 1.00 |
| HMW HA (2x10⁶) | 200 | 1.19 ± 0.23 | 1.37 ± 0.54 | 1.27 ± 0.19 | 1.04 |
| | 2 | 1.14 ± 0.14 | 1.54 ± 0.52 | 1.10 ± 0.10 | 0.93 |
| LMW HA (2x10⁵) | 200 | 0.98 ± 0.16 | 1.00 ± 0.05 | 1.04 ± 0.13 | 0.66 |
| | 20 | 0.54 ± 0.26 | 0.59 ± 0.03 | 0.60 ± 0.02 | 0.71 |
| | 2 | 0.61 ± 0.08 | 0.62 ± 0.03 | 0.59 ± 0.06 | 0.61 |
| | 0.2 | 0.54 ± 0.15 | 0.49 ± 0.02 | 0.20 ± 0.06 | 0.52 |
| VLMW HA (2x10⁴) | 200 | 0.36 ± 0.02 | 0.28 ± 0.15 | 0.46 ± 0.01 | 0.37 |
| | 2 | 0.45 ± 0.01 | 0.39 ± 0.25 | 0.48 ± 0.02 | 0.16 |
| HA Oligomers (4-mers, pure) | 0.2 | 1.63 ± 0.07 | 2.14 ± 0.02 | 7.81 ± 1.91 | 4.76 ± 0.10 |
| HA Oligomers (4-mer, mixture) | 0.2 | 1.82 ± 0.26 | 2.2 ± 0.00 | 7.49 ± 1.48 | 4.57 ± 0.11 |

Figure 1

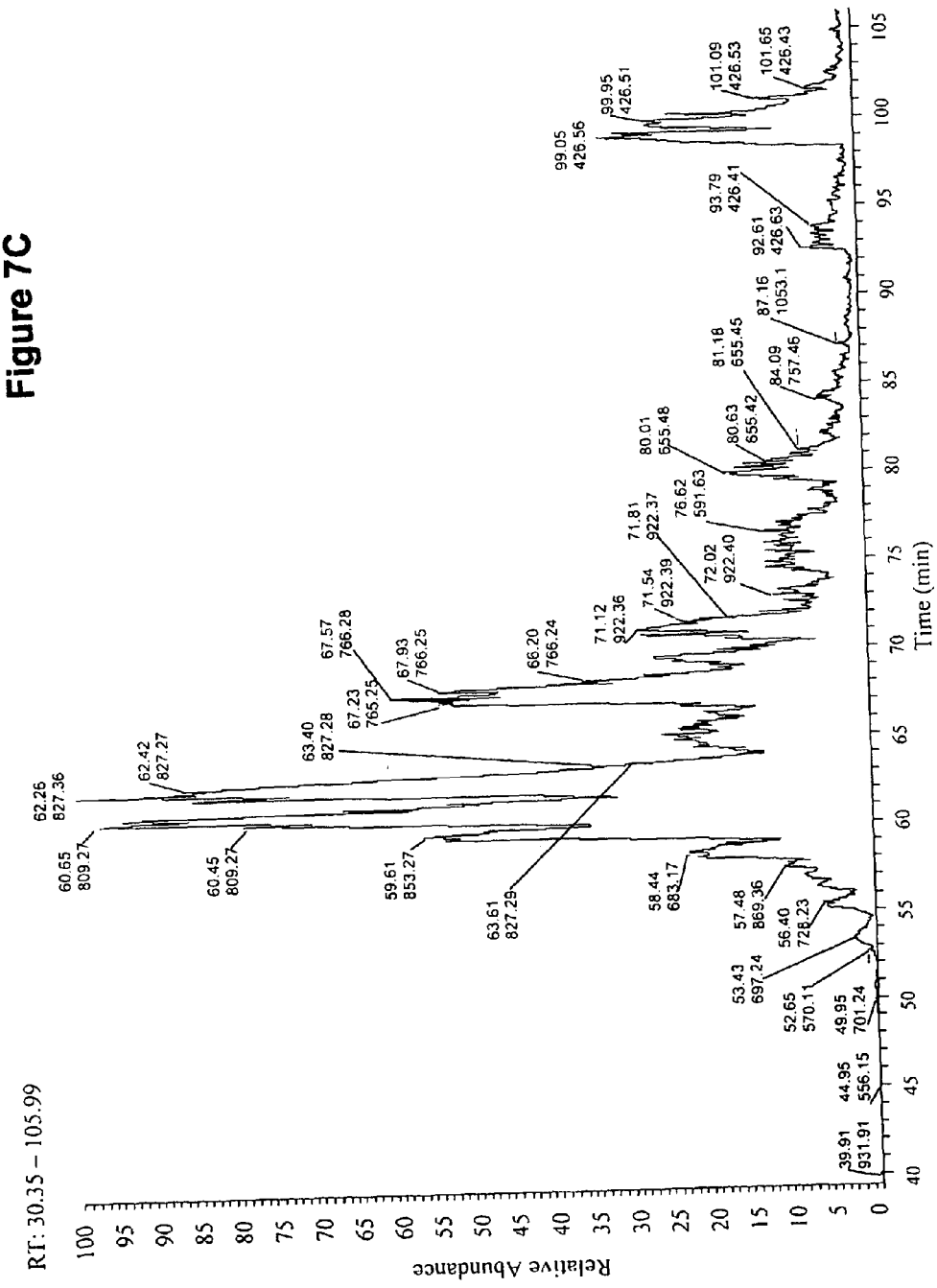

| | | Changes with respect to pure control | |
|---|---|---|---|
| | | 4-mer | 20kDa HA |
| TGF-β | DNA | ↓↓ | ↓↓ |
| | Collagen | ↑↑ | = |
| | Tropoelastin | ↑↑ | ↑↑ |
| | Total Matrix | ↑↑ | ↓ |
| | Total Elastin | ↑↑ | ↓ |
| IGF-1 | DNA | ↑ | ↓ |
| | Collagen | = | ↑↑ |
| | Tropoelastin | ↓ | ↑↑ |
| | Total Matrix | = | ↑↑ |
| | Total Elastin | ↓ | ↑↑ |

Figure 8A

| Biochemical outcomes/ng DNA | No HA | HA Oligomers | TGF-β1 addition | | |
|---|---|---|---|---|---|
| | | | VLMW HA | LMW HA | HMW HA |
| Proliferation ratio | = | ↓ | = | = | ↔ |
| Total collagen | ↑ | ↑↑ | ↑ | ↑ | → |
| Tropoelastin | = | ↑↑ | ↑ | ↑ | → |
| Matrix elastin | ↑ | ↑↑ | ↑ | ↔ | → |
| Total elastin | ↑ | ↑↑ | ↑ | ↑ | → |

Figure 8B

| HA Size (Daltons) | Dose (µg/mL) | Proliferation ratio at 21 days relative to control | Increase in tropoelastin/DNA with respect to control | Increase in soluble elastin/DNA with respect to control | Increase in insoluble elastin/DNA with respect to control | Increase in matrix elastin/DNA with respect to control |
|---|---|---|---|---|---|---|
| Oligomers | 2 | 0.92 ± 0.001 | 1.82 ± 0.26 | 2.08 ± 0.36 | 7.49 ± 1.48 | 2.65 ± 0.05 |
| Oligomers | 0.2 | 0.79 ± 0.018 | 1.48 ± 0.23 | 1.39 ± 0.18 | 0.65 ± 0.07 | 1.08 ± 0.13 |
| Oligomers + TGF-β | 0.2 | 0.13 ± 0.004 | 8.01 ± 0.16 | 8.88 ± 1.87 | 5.48 ± 0.36 | 7.47 ± 1.24 |
| Oligomers + IGF1 | 0.2 | 1.37 ± 0.021 | 0.79 ± 0.03 | 1.04 ± 0.23 | 0.46 ± 0.1 | 0.8 ± 0.17 |

Figure 9

| | Total matrix elastin synthesized/DNA, ng/ng (alkali soluble + insoluble elastin) | Matrix elastin/total elastin, % | Insoluble elastin/total matrix elastin, % |
|---|---|---|---|
| Control | 5624 ± 536 | 36.8 | 7.1 ± 0.8 |
| IGF-1 alone | 9533 ± 1282 | 33.9 | 3.8 ± 1.4 |
| HA Oligomers + IGF1 | 5432 ± 1190 | 46.6 | 24 ± 5.2 |
| VLMW HA + IGF1 | 12477 ± 896 | 36.3 | 6.8 ± 0.4 |
| LMW HA + IGF1 | 9953 ± 1089 | 34.3 | 14.2 ± 1.5 |
| HMW HA + IGF1 | 6663 ± 677 | 38.3 | 29.5 ± 4.6 |

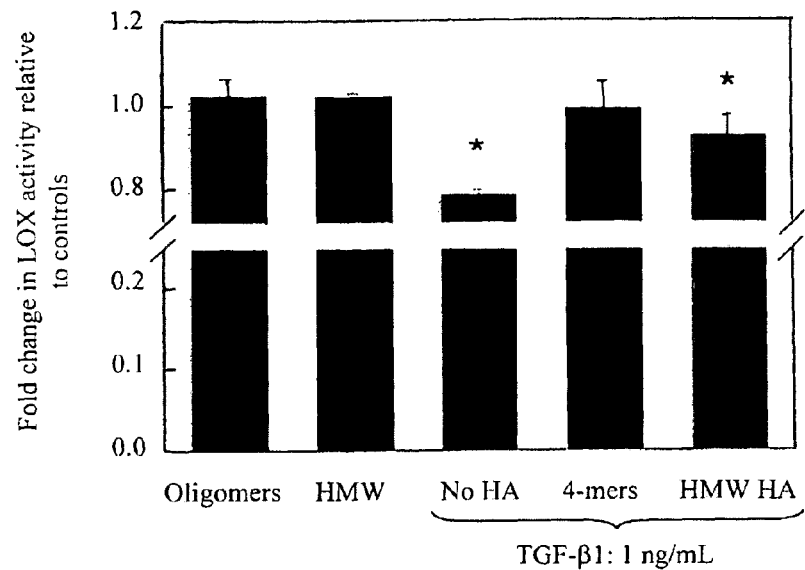
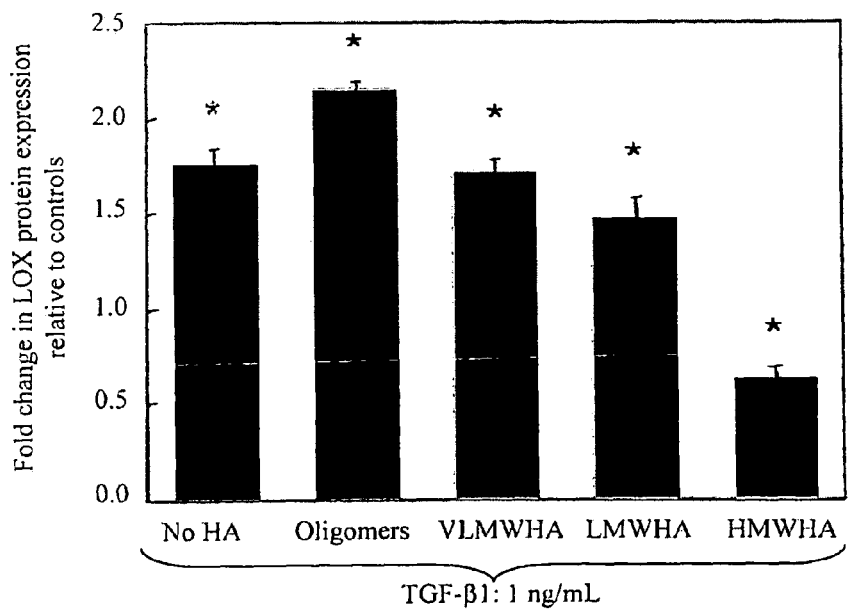

| Cu Nanoparticle dose | 0.01 M | | | |
| --- | --- | --- | --- | --- |
| | No HA | HA 4-mer | | |
| DNA | 1.54 ± 0.15 | 1.34 ± 0.32 | | |
| Tropoelastin | 0.70 ± 0.04 | 0.38 ± 0.07 | | |
| Insoluble Matrix Elastin | 0.62 ± 0.04 | 2.70 ± 0.18 | | |
| Matrix/Total elastin | 0.99 ± 0.02 | 1.77 ± 0.17 | | |
| LOX activity | 1.09 ± 0.02 | 1.15 ± 0.01 | | |
| LOX synthesis | 1.11 ± 0.13 | 1.29 ± 0.16 | | |
| CuSO$_4$ dose | 0.01 M | | 0.1 M | |
| | No HA | HA 4-mer | No HA | HA 4-mer |
| DNA | 1.94 ± 0.3 | 1.4 ± 0.2 | 0.24 ± 0.1 | 0.20 ± 0.1 |
| Tropoelastin | 0.51 ± 0.01 | 0.73 ± 0.1 | 4.14 ± 0.1 | 5.44 ± 0.7 |
| Insoluble Matrix Elastin | 0.6 ± 0.1 | 1.23 ± 0.3 | 4.20 ± 0.7 | 5.80 ± 0.80 |
| Matrix/Total elastin | 0.98 ± 0.1 | 1.04 ± 0.04 | 1.00 ± 0.0 | 0.86 ± 0.1 |
| LOX activity | 1.4 ± 0.2 | 1.12 ± 0.14 | 1.09 ± 0.2 | 1.19 ± 0.3 |
| LOX synthesis | 0.76 ± 0.1 | 0.92 ± 0.10 | 1.30 ± 0.2 | 1.35 ± 0.1 |

ELASTOGENIC CUES AND METHODS FOR USING SAME

CROSS REFERENCE TO RELATED APPLICATION

The present application claims filing benefit of U.S. Provisional Patent Application Ser. No. 60/890,934 having a filing date of Feb. 21, 2007, which is incorporated herein in its entirety.

FEDERALLY SPONSORED RESEARCH AND DEVELOPMENT

The United States Government may have rights to the information disclosed herein pursuant to grants from the National Science Foundation (0132573), the National Institutes of Health (EB 0006078-01A1), and the National Center for Research Resources (CO6RR018823).

BACKGROUND

The extracellular matrix (ECM) within native tissues consists predominantly of cross-linked elastin and collagen that contribute to the biologic and mechanical properties of the tissue. Various factors can compromise tissue homeostasis including congenital absence or degradation of elastin and malformation of elastin as well as limited elastin regeneration following damage caused by, e.g., disease or surgical procedures, due to innately poor elastin synthesis by adult vascular cells.

Elastin is a key component of the ECM that allows the matrix to stretch and retract following mechanical loading and release. Vascular smooth muscle cells (SMCs) typically synthesize elastin as a soluble tropoelastin, which is then post-translationally cross-linked by lysyl oxidase to form an insoluble matrix. In addition to providing structural support and suppleness to the tissue, elastin is also critical in regulating SMC behavior, especially during vascular morphogenesis and disease. Thus, mechanical disruption of the vascular elastin matrix, e.g., progressive damage due to conditions such as atherosclerosis or aneurysm, the congenital absence of elastin or deformation of the elastin matrix, for instance due to surgical procedures such as angioplasty, can severely compromise vascular homeostasis.

One of the aims of current research in tissue engineering is to generate, both in vivo and ex vivo, for instance as graft materials, functional blood vessels and cardiac tissue (e.g., heart valve tissue). The attainment of this goal requires the ability to create structurally and functionally-faithful vascular elastic matrices. Unfortunately, many challenges related to adequate mechanical strength and long-term functionality still remain to be solved. One of the reasons for limited progress to date is the unavailability of materials, e.g., cues, that can up-regulate innately poor elastin synthesis by adult vascular cells. Another problem that must be overcome is the tendency of vascular cells to become hyper-prolific during inflammatory vascular disease, which often accompanies the disease states that compromise tissue homeostasis due to lack of a healthy elastin network in the tissue.

Previous studies have suggested that use of hyaluronan (HA) based matrices in smooth muscle cell (SMC) development may improve elastin synthesis, maturation, and stabilization (Ramamurthi, et al., _Biomaterials_ 26 (2005) 999-1010). Further research into the possible use of HA in vascular tissue engineering applications has shown that UV surface modification of HA-based matrices does not significantly alter inherently poor platelet binding characteristics of HA gels, nor do the treated matrices show any increase in thrombogenic characteristics (Amarnath, et al., _Biomaterials_ 27 (2006) 1416-1424). However, when the HA matrices were examined for elastogenic effects, long-chain HA (MW>1×$10^6$ Da), and large fragments (MW>2×$10^4$ Da) either had little or no effect or even significantly inhibited total and crosslinked elastin matrix synthesis (Joddar, et al., _Biomaterials_ 27 (2006) 2994-3004, FIG. 1).

What are needed in the art are materials that can be utilized in tissue engineering applications to encourage the development of functional and structurally sound connective tissues (e.g., cardiovascular tissues) characterized by a well-developed elastin matrix structure.

SUMMARY

In one embodiment, disclosed is a composition comprising one or more elastogenic cues for upregulating elastin synthesis. For example, elastogenic cues can include hyaluronic acid oligomers. For instance, the hyaluronic acid oligomers of a composition can be less than about 12 monomer units in length. An elastogenic composition can also include a delivery vehicle for delivering the elastogenic cues, e.g., the hyaluronic acid oligomers, to a cellular construct including elastin producing cells.

According to another embodiment, disclosed is an elastogenic composition comprising hyaluronic acid fragments in conjunction with a growth factor.

For instance, hyaluronic acid oligomers of a composition can have a number average molecular weight of less than about 1×$10^4$ Daltons.

According to another embodiment, an elastogenic composition is disclosed including as elastogenic cues nanostructures that include a source of copper ions. For instance, an elastogenic composition can include copper-containing nanostructures that can provide copper ions to a cellular construct in a concentration between about 0.1 micromolar ($\mu$M) and about 0.1 molar (M).

Methods for upregulating elastin synthesis by elastin producing cells through utilization of disclosed elastogenic cues and compositions incorporating the disclosed elastogenic cues are also disclosed herein. For instance, a method can include contacting a cellular construct including elastin producing cells with an elastogenic composition as described herein.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which:

FIG. 1 is a summary of the results of the biochemical effects of variously sized HA materials on development of tropoelastin and matrix elastin in an SMC culture;

FIGS. 7A-7C illustrate the MS spectra of peptide analysis for aortal tissue (FIG. 7A), tissue culture developed on a matrix including exogenous HA oligomers (FIG. 7B), and tissue culture developed on a matrix including tethered HA oligomers (FIG. 7C);

FIGS. 8A and 8B summarize the results of the biochemical effects of concurrent delivery of TGF-β or IGF-1 with HA of various sizes on cultures of SMC;

FIG. 9 is a summary of the elastogenic effects on SMC cultures developed with HA oligomers at two different concentrations and also with concurrent delivery of TGF-β or IGF1;

FIGS. 14A and 14B illustrate lysyl oxidase (LOX) enzyme activities (FIG. 14A) and LOX protein synthesis (FIG. 14B) in test cultures at 16 day culture periods;

FIG. 25 summarizes the effects on LOX production and activity through addition of copper ions via copper sulfate or copper nanoparticles.

DETAILED DESCRIPTION

Figure 2:
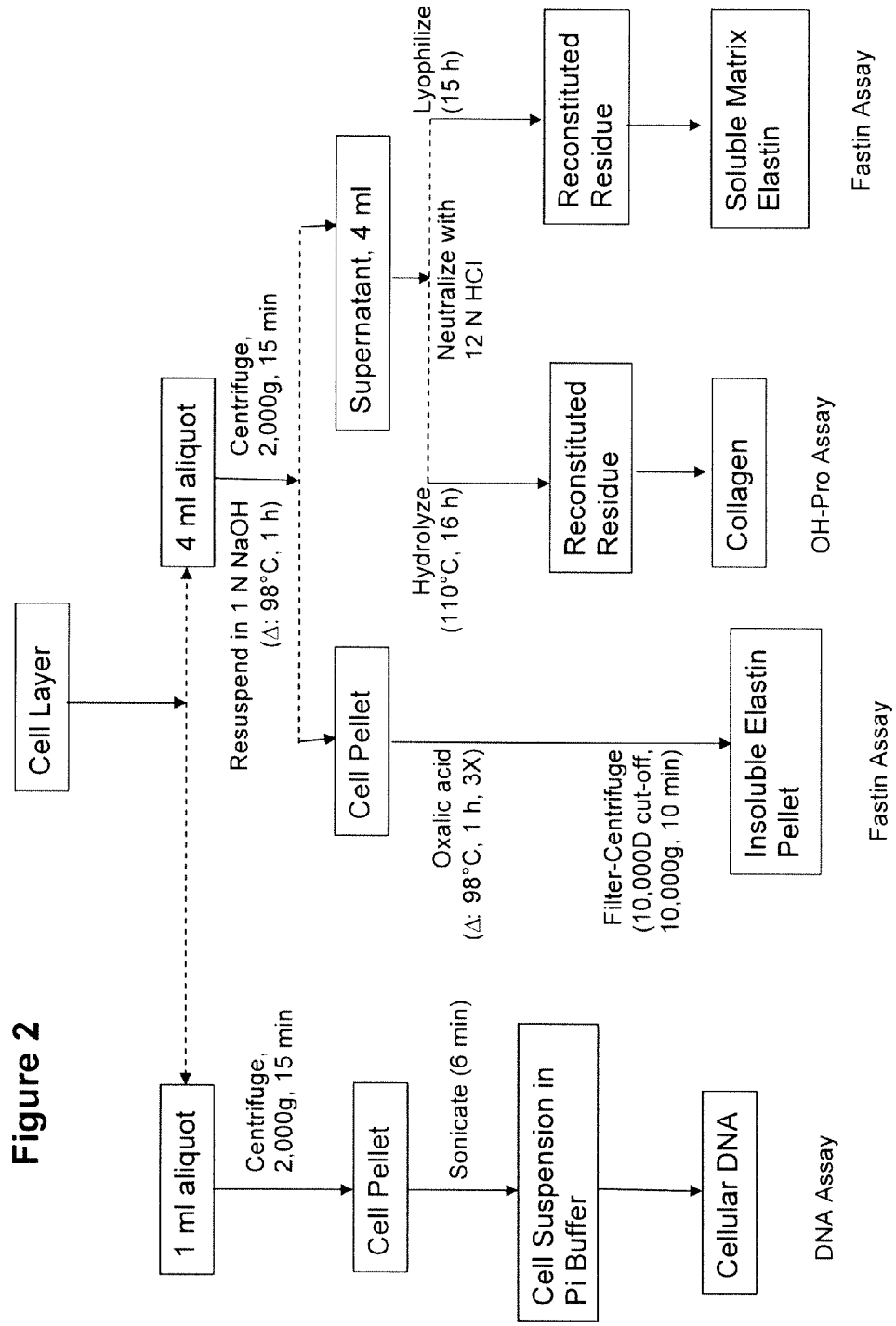
FIG. 2 is a flow diagram illustrating the biochemical analyses carried out in Example 1.

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

The present disclosure is generally directed to elastogenic cues that can be beneficially employed in development and stabilization of tissues, i.e., any elastin-containing tissue. For example, disclosed material can be utilized to regenerate and/or stabilize cardiovascular tissue, dermal tissue, pulmonary tissue and the like. Disclosed elastogenic cues can upregulate soluble tropoelastin synthesis and/or insoluble matrix elastin formation in any elastin-producing cells. For instance, the disclosed materials can up-regulate elastin matrix synthesis by vascular cells, and in one particular embodiment by adult vascular smooth muscle cells (SMCs). Other cells that can respond to disclosed cues as described herein can include, without limitation, fibroblasts, endothelial cells, and valvular interstitial cells Beneficially, in addition to encouraging synthesis of elastin in a cellular matrix, disclosed materials can also stabilize an ECM matrix through suppression of elastin-laminin receptor (ELR), upregulation of which has been associated with elastin degradation associated with matrix metalloproteinase (MMP) activity as well as in ECM remodeling found in aging and atherosclerosis. In addition, disclosed materials can inhibit cell hyper-proliferation (e.g., hyperplasia), which often occurs in inflammatory vascular disease accompanying many of the disease states that lead to destruction of the elastin matrix, e.g., damage due to surgical procedures, chronic vascular disease, and the like. Disclosed materials can also encourage organization of synthesized elastin into elastin fibrils and fibers as well as upregulate expression of LOX and promote crosslinking and formation of insoluble elastogenic matrices.

According to one embodiment of the present disclosure, materials including specifically-sized HA oligomers and polymers as elastogenic cues can be provided that can upregulate tropoelastin synthesis by cells, and in one particular embodiment, by SMCs, e.g., by adult vascular SMCs. Increased production of soluble tropoelastin by SMCs can in turn lead to increased production of both secondary molecular elastin structures, i.e., cross-linked structures including rigid α-helical segments containing the cross-link sites and elastic hydrophobic domains formed of the β-sheets, and macro-elastin structures composed of a central elastin core surrounded by microfibrils.

Hyaluronic acid (HA, equivalently termed hyaluronan or hyaluronate throughout this disclosure) is a non-sulfated glycosaminoglycan polysaccharide including alternating D-glucuronic acid and D-N-acetylglucosamine units, linked together via alternating β-1,4 and β-1,3 glycosidic bonds and having the following general structure:

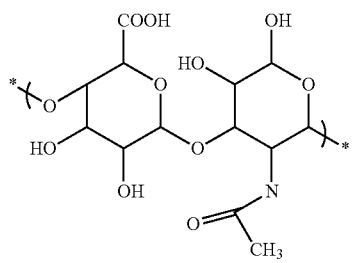

HA naturally occurs as a large molecule. Polymers of hyaluronan can range in size from 5 to 20,000 kDa in vivo and occur in a variety of connective tissues including spinal, ocular, and synovial fluid, as well as in skin, articular cartilage, and cardiovascular tissues.

According to one embodiment, HA oligomers of less than about 12 monomer units (6 disaccharide units) are disclosed as elastogenic cues for use in developing and/or stabilizing elastin-containing tissue. For instance, a composition as disclosed herein can include a mixture of HA oligomers, or can include only HA oligomers of a particular size. For instance, in one embodiment, a composition can include an HA oligomer mixture including a random distribution of oligomers of a size less than about 12-mers.

In another embodiment, a composition can include a mixture of cues, for instance a mixture of different oligomers, all of which can be within a close size distribution. For instance, a composition can include a mixture of 2-mers up to about ti-mers, a mixture of 4-mers up to about 8-mers, and the like.

In another embodiment, a composition can include a significant fraction of oligomers of a particular size. For example, a composition can include a mixture of different-sized oligomers, and greater than about 75% w/w of the mixture can be of a single size.

In yet another embodiment, a composition can include substantially all oligomers of a single size. For instance, more than about 99% w/w of the oligomers of a composition can be of the same size. For example, a composition can include an HA oligomer preparation, in which more than about 99% w/w of the oligomers are 4-mers.

HA oligomers as may be utilized as elastogenic cues in the disclosed compositions are available commercially (e.g., Associates of Cape Cod, East Falmouth, N.J.) or may be prepared via enzymatic digestion of HA polymers according to standard methods as are generally known in the art, examples of which are described in more detail below.

HA oligomers and polymers of a predetermined size have also shown efficacy in development of elastin-containing cellular constructs when delivered in conjunction with one or more secondary additives. For instance, in one embodiment, HA oligomers and/or polymers can be delivered in conjunction with a growth factor. For example, a composition can include HA of a size less than about 200 kDa in conjunction with a growth factor. In one embodiment, low molecular weight HA of a size between about 100 kDa and 500 kDa can be combined with one or more growth factors to form an elastogenic composition as described herein. In another embodiment, very low molecular weight HA of a size between about 1 kDa and about 0.6 kDa can be combined with one or more growth factors to form an elastogenic composition. For instance, HA oligomers as described above can be combined with one or more growth factors to form an elastogenic composition.

Growth factors encompassed by the present disclosure can include transforming growth factors, insulin-like growth factors, and the like. For instance, a composition can include IGF-I, IGF-II, TGF-β I through III, including the TFG-β superfamily, or a combination thereof in combination with HA fragments and/or oligomers of a size less than about 500 kDa in size.

Addition of a growth factor to disclosed compositions can further improve elastin matrix synthesis in a cellular construct. For instance, and while not wishing to be bound by any particular theory, a composition including TGF-β in conjunction with HA oligomers can increase production of soluble tropoelastin by cells of the construct as well as increasing production of LOX, which catalyzes crosslinking of the matrix. Thus, a composition including various combinations of elastogenic cues and additives as disclosed herein can enhance the crosslinking of soluble tropoelastin into matrix elastin and further improve formation of an elastogenic matrix.

In one embodiment, a composition can include a component that can further encourage crosslinking of soluble tropoelastin to form an insoluble elastogenic matrix. For instance, a composition can include elastogenic cues in addition to or other than HA and/or growth factors that can enhance production and/or activity of lysyl oxidase (LOX) enzyme. LOX enzyme is an extracellular copper dependent enzyme that oxidizes primary amines on lysine residues of tropoelastin and procollagen to form allysine, an aldehyde, and thus catalyzes desmosine crosslinking of the extracellular matrix proteins through condensation and subsequent formation of crosslinked networks.

As is generally known in the art, LOX availability and activity is dependent upon the presence of copper ions ($Cu^{2+}$). Accordingly, in one embodiment, a composition as disclosed herein can include a copper-containing component that can provide copper ions to a delivery site.

While not wishing to be bound by any particular theory, it is believed that delivery of copper ions to a cellular construct as described herein can improve formation of insoluble elastin matrix according to two different modes. First, it is believed that copper ions may enhance endogenous production of TGF-β, which in turn can upregulate production of LOX enzyme. In addition, it is believed that cell layer localized exogenous HA can electrostatically associate with both copper ions and tropoelastin to non-transiently upregulate the elastin crosslinking mechanism. In addition, copper ions can improve the extent and efficiency of crosslinking of elastin precursors by enhancing extracellular transport of endogenous LOX as well as by increasing functional activity of endogenous and exogenous LOX through enablement of electron transfer from oxygen.

This can facilitate oxidative deamination of lysyl groups in elastin and collagen, leading to formation of crosslinks. Thus, delivery of copper ions to a cellular construct can encourage formation of insoluble elastogenic extracellular matrices even when delivered without the addition of HA fragments in a composition. Accordingly, in one embodiment, a composition as disclosed herein can include a component for delivery of copper ions as an elastogenic cue to a cellular construct, and this elastogenic cue can be delivered either in conjunction with other elastogenic cues, e.g., HA fragments, or without other elastogenic cues, as desired.

A copper-containing component suitable for use as described herein can include any material that can deliver copper ions to a natural or synthetic cellular construct. For instance, in one embodiment, a copper salt can be utilized such as, without limitation, copper sulfate or copper chloride. In general, copper ions can be delivered to a site in an amount of between about 0.1 µM and about 0.1 M, for instance about 0.1M, in one preferred embodiment.

In one embodiment, a highly-controlled delivery scheme may be utilized to deliver copper ions to a cellular construct, for instance when long-term exposure to copper ions is desired, so as to limit or prevent cytotoxicity due to high steady-state levels of copper ions. For instance, in one embodiment, particles including metallic copper that can release copper ions upon oxidation in an aqueous environment can be utilized. For instance, copper-containing particles formed on a nanometer scale, e.g., less than about 500 nm in diameter, can be provided to a cellular construct as an elastogenic cue component of a composition as disclosed herein. It should be understood, however, that the size of the nanostructures may vary. For instance, the average size (e.g., diameter) of the particles may range from about 1 nanometers (nm) to about 500 nm, and in some embodiments, from about 1 nm to about 200 nm, and in some embodiments, from about 60 nm to about 120 nm.

The shape of copper-containing nanostructures as may be utilized as disclosed herein may generally vary. In one preferred embodiment, for instance, a copper-containing particle can be spherical in shape. However, it should be understood that other shapes are also contemplated by the present disclosure, such as cubes, plates, rods, discs, bars, tubes, irregular shapes, etc.

In addition, while copper-containing nanostructures can be pure copper in one preferred embodiment, this is not a requirement of the disclosed subject matter and in other embodiments, nanostructures including copper in conjunction with other materials can be utilized. Copper nanoparticles can be obtained from sources such as, for instance, the American Elements Company, or can be manufactured according to any known formation process including, without limitation, microwave irradiation, thermal decomposition, or microemulsion methods.

Compositions including HA, optionally in conjunction with one or more other elastogenic cues or other additives, can include any of a variety of delivery vehicles for delivering the materials to a natural or synthetic cellular construct. In general, the preferred route for delivery of elastogenic cues as described herein will depend upon the specific application. For example, the disclosed materials can be provided for in vivo use, for instance in treatment of damaged or diseased cardiovascular tissue, and can be provided in a delivery vehicle designed to encourage the growth and development of healthy tissue at a particular site of damage. Optionally, elastogenic cues can be provided for in vivo systemic delivery, for example to provide the elastogenic cues throughout a portion of or even all of the cardiovascular system.

It should be understood, however, that the disclosed elastogenic cues and compositions are not limited to in vivo use. In one embodiment, disclosed materials can be provided in conjunction with a suitable delivery vehicle so as to encourage growth and development of an in vitro or ex vivo elastogenic cellular construct that may be utilized, for example, in developing implantable graft materials or in obtaining cellular expression products, e.g., protein expression products including antibodies and the like.

In general, elastogenic cues as described herein can be provided as a component of a biocompatible composition. For instance, compositions disclosed herein can include HA oligomers or polymers, optionally in combination with growth factors and/or a source of copper ions, in a concentration that can vary over a wide range, with a preferred concentration generally depending on the particular application and the nature of the cellular construct to which the elastogenic cues will be supplied. For example, in one embodiment, a composition of the invention can include HA oligomers or polymers at a concentration of from about 0.2 µg/ml to about 200 µg/ml.

A composition can include one or more growth factors at a total concentration that can generally vary according to the specific growth factor utilized. For example, TGF-β can generally be included at a concentration of about 1 ng/ml, while IGF-1 can be included at a concentration of about 500 ng/ml. Such variations and concentrations are well known to one of ordinary skill in the art. It should be noted that while these exemplary concentrations are effective in certain embodiments, the disclosed materials can be provided at a wider range of concentrations.

In one embodiment, a composition can include elastogenic cues provided on a biocompatible scaffold that may be utilized as a delivery vehicle for the elastogenic cues. In general, any tissue engineering scaffolding material as is known in the art can be utilized. For instance, elastogenic cues can be provided on a single continuous scaffold or a scaffold formed of multiple discrete constructs.

For purposes of the present disclosure, the term 'continuous scaffold' generally refers to a material suitable for use as a cellular anchorage that can be utilized alone as a single, three-dimensional entity. A continuous scaffold is usually porous in nature and can have a fixed or semi-fixed shape (e.g., it may be somewhat flexible). Continuous scaffolds are well known in the art and can be formed of many materials, e.g., coral, collagen, calcium phosphates, synthetic polymers, hydrogels and the like, and are usually pre-formed to a specific shape designed for the location in which they will be placed. Continuous scaffolds can be seeded with cells through absorption and cellular migration, often coupled with application of pressure through simple stirring, pulsatile perfusion methods or application of centrifugal force.

Discrete constructs, a plurality of which can form a scaffold, are generally relatively small articles, such as beads, rods, tubes, fragments, or the like. When utilized as a cellular scaffold, a plurality of identical or a mixture of differently shaped discrete constructs can be loaded with cells and located as desired to function as a single cellular scaffold. Exemplary scaffolds formed of a plurality of discrete constructs suitable for use in the present disclosure are described further in U.S. Pat. No. 6,991,652 to Burg, which is incorporated herein by reference.

Suitable materials for a biocompatible scaffold are generally known in the art, and preferred materials for any particular scaffold will generally depend at least upon the primary purpose of the scaffold. For example, in one embodiment, a biocompatible scaffold can be formed from biodegradable materials. In other embodiments, more permanent biocompatible structures formed from non-degradable materials can be utilized. For instance, polymers that display little or no biodegradability such as polystyrenes, polyurethanes, ultra high molecular weight polyethylenes (UHMWPE), and the like, can be utilized to form a scaffold.

In addition, suitable scaffolding materials can be synthetic or naturally derived materials. For instance, a scaffold can include any of a number of exemplary synthetic polymers such as polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, and the like, and copolymers of the same. Optionally, a scaffold can include naturally derived materials including, but not limited to chitosan, agarose, alginate, collagen, hyaluronic acid, and carrageenan (a carboxylated seaweed polysaccharide), demineralized bone matrix, and the like, and copolymers of the same.

In one preferred embodiment, a biocompatible scaffold for use with the disclosed elastogenic cues can be based upon HA. Exemplary HA gels as may be used are disclosed, for example, in U.S. Pat. No. 4,582,865 to Balazs, et al., which is incorporated herein in its entirety. Hyaluronan-based crosslinked gels can be preferred as scaffolding material in some embodiments as HA composes a larger percentage of total GAGs in many tissues and as such, an HA scaffold can be relatively biocompatible as well as lowly antigenic and immunogenic, particularly due to the structural homology of the HA molecule across species.

In one embodiment, a scaffold can be surface-treated to improve growth and development of a cellular construct on or adjacent to the scaffold. For instance, a hydrogel scaffold such as an HA scaffold can be surface treated with UV radiation as described by Amarnath, et al., *Biomaterials* 27 (2006) 1416-1424, which is incorporated herein by reference. UV surface modification of HA-based matrices has been shown to not significantly alter the inherent poor platelet binding characteristics of HA gels, nor do the treated matrices show any increase in thrombogenic characteristics. One exemplary UV surface modification process can include irradiating a formed gel with UV $\lambda \cong 254$ nm) for about 24 hours in a biological hood.

Elastogenic cues can be loaded onto the scaffold according to any suitable process. For instance, HA oligomers or polymers can be tethered to a scaffolding material or can be encapsulated in a scaffold as an exogenous material, as desired. For instance, the tethering of HA oligomers may be preferred in one embodiment as, while the mode of presentation of HA oligomers does not appear to influence the impact of the composition on cell proliferation or elastin synthesis, utilization of tethered oligomers over exogenous oligomers can generate greater amounts of desmosine crosslinks in a generated elastin matrix (see, e.g., Joddar, et al., Biomaterials, 28 (2007) 3918-3927, which is incorporated herein by reference).

There are numerous methods well known in the art for encapsulating a material in a scaffold as may be utilized in the present disclosure. For example, a polymeric scaffold can be loaded with elastogenic HA materials by development of a crosslinked matrix in the presence of the HA materials. In another embodiment, a preformed scaffold can be held in a solution including the HA materials and the scaffold can be loaded via diffusion of the elastogenic cues in to the scaffold over a suitable period of time.

As mentioned, HA oligomers can be tethered to scaffolds. According to one such embodiment, a scaffold can be formed or treated so as to provide a reactive functionality on the scaffold matrix. For example, a scaffold matrix material can be aminated and HA oligomers can be tethered to the matrix via carbodiimide linking chemistry, as is known in the art. A scaffold can be functionalized with any suitable reactive functionality, including, without limitation, carboxylic acid, hydroxy, aldehyde, thiol, or ester groups, that may be utilized in tethering HA oligomers, which may also be functionalized as desired, to a scaffold matrix.

In one embodiment, a scaffold can be loaded with living cells, e.g., SMCs, following loading of one or more elastogenic cues so as to encourage the growth and development of an elastogenic cellular construct on the scaffold. For instance, SMCs can be loaded on a scaffold in the form of a multi-cellular construct that can be a naturally derived construct or a tissue-engineered construct. Optionally, individual cells can be seeded on or in a scaffold, for instance via absorption and cellular migration, optionally coupled with application of pressure through simple stirring, pulsatile perfusion methods or application of centrifugal force. Such embodiments can be useful to, for instance, examine and study the long term growth and development of a tissue, to develop an elastogenic tissue suitable for implant, or to obtain a cellular-derived product from the cellular construct.

In another embodiment, a delivery vehicle can be loaded with disclosed elastogenic cues and utilized in vivo. For instance, elastogenic cues can be loaded in a delivery vehicle via encapsulation, coating, infusion, or any other loading mechanism as is known in the art. In one embodiment, a delivery vehicle can be utilized to target delivery of the elastogenic cues to a specific site, such as a damaged blood vessel, e.g., using a minimally invasive procedure to provide long-term delivery of the elastogenic cues from a biocompatible implantable device. For example, perivascular or endovascular routes of delivery could be utilized for local targeted delivery of the disclosed elastogenic cues.

Perivascular delivery technologies suitable for use are generally known to those of skill in the art, and thus need not be explained at length herein. For instance, exemplary known perivascular drug delivery technologies include those described by Chen, et al. (U.S. Patent Application Publication No. 2005/0079202) and Nathan (U.S. Patent Application Publication No. 2003/0228364), both of which are incorporated herein by reference. These exemplary perivascular delivery systems include a polymeric delivery vehicle that can be injected or directly placed, for instance via surgery, at a particular location outside of a blood vessel so as to provide controlled release of elastogenic cues encapsulated or otherwise loaded therein into the blood vessel wall over a period of time.

Many endovascular drug delivery methods are likewise known in the art. For example, DiCarlo, et al. (U.S. Pat. No. 6,929,626, incorporated herein by reference) describes an intraluminally placeable tubular device that can be located within the lumen of a blood vessel and coated or otherwise loaded with one or more elastogenic cues described herein. The tubular member includes yarns interconnected in a pattern defining opposed interior and exterior textile surfaces. At least one of the textile surfaces is the body fluid-contacting luminal surface or the body lumen-contacting exterior surface.

Wu, et al. (U.S. Pat. No. 6,979,347, incorporated herein by reference) describes an apparatus and associated method as may be utilized for delivering a therapeutic substance such as disclosed elastogenic cues to a vascular lumen. Specifically, an implantable prosthesis, such as a stent, can be utilized that has grooves or trenches formed thereon. The grooves are formed on specific regions of the stent struts to increase the flexibility of the stent. The grooves also provide a location for carrying elastogenic cues for delivery from the device following implantation. For example, elastogenic cues can be deposited directly in to the grooves using conventional spray or modified dip techniques.

In one embodiment, elastogenic cues can be delivered via timed release or sustained release delivery systems as are generally known in the art. Such systems can be desirable, for instance, in situations where long term delivery of the materials to a particular organ or vascular location is desired. According to this particular embodiment, a sustained-release matrix can include a matrix made of materials, usually polymers, which are degradable by enzymatic or acid/base hydrolysis or by dissolution. Once located at or near the target tissue, e.g., inserted into the body, for instance in the form of a patch or a stent, the matrix can be acted upon by enzymes and body fluids. The sustained-release matrix can be chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Possible biodegradable polymers and their use are described, for example, in detail in Brem et al. (1991, *J. Neurosurg.* 74:441-6), which is hereby incorporated by reference in its entirety.

In one embodiment, elastogenic cues can be provided on a hydrogel delivery vehicle. Hydrogels are herein defined to include polymeric matrices that can be highly hydrated while maintaining structural stability. Suitable hydrogel matrices can include un-crosslinked and crosslinked hydrogels. In addition, crosslinked hydrogel delivery vehicles can include hydrolyzable portions, such that the matrix can be degradable when utilized in an aqueous environment, e.g., in vivo. For example, the delivery vehicle can include a cross-linked hydrogel including a hydrolyzable cross-linking agent, such as polylactic acid, and can be degradable in vivo.

Hydrogel delivery vehicles of the present disclosure can include natural polymers such as glycosaminoglycans, polysaccharides, proteins, and the like, as well as synthetic polymers, as are generally known in the art. A non-limiting list of hydrophilic polymeric materials that can be utilized in forming hydrogels can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like. In one preferred embodiment, a hydrogel delivery vehicle can include an HA-based scaffold, as discussed above.

Hydrogel delivery vehicles can be formed according to any method as is generally known in the art. For instance, the hydrogel can self-assemble upon contact of the various components or upon contact in conjunction with the presence of particular environmental conditions (such as temperature or pH). Alternatively, assembly can be induced according to any known method following combination of the components. For example, step-wise or chain polymerization of multifunctional monomers, oligomers, or macromers can be induced via photopolymerization, temperature dependent polymerization, and/or chemically activated polymerization. Optionally, the hydrogel can be polymerized in the presence of an initiator. For example, in one embodiment, the hydrogel can be photopolymerized in the presence of a suitable initiator such as Irgacure® or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used.

In another embodiment, a polycationic polypeptide such as polylysine or polyarginine can be utilized as an initiator.

The components of the hydrogel delivery vehicle can also be designed so as to provide a self-assembling delivery vehicle. For example, a hydrogel precursor can be administered to a subject, and the hydrogel matrix can self-assemble at physiological conditions following administration of the precursor. For instance, the hydrogel precursor can include self-assembling biopolymers such as collagens, laminins, pro-elastin peptides, and the like. Optionally, a self-assembling hydrogel precursor can include synthetic polymers that can array themselves according to domains, as is generally known in the art. For example, hydrophilic, relatively charge-neutral synthetic polypeptides such as polyglycine or polylysine can be modified to function in this capacity. Polypeptides can be crosslinked by using carboxy-activating crosslinking agents such as water-soluble carbodiimides. Such cross-linking agents can be used to attach self-assembling proteins or other self-assembling macromolecules to the polypeptides. One example of this approach includes formation of a carbodiimide linkage of collagen or laminin with polylysine. Other hydroxylated entities can be linked in a similar manner. For example, in one embodiment, polyvinyl alcohol can be linked with polypeptides using an epoxy-activation approach or crosslinked via polymerizable methacrylate groups along its side chains, as is known in the art.

In another embodiment, a self-assembling hydrogel can be generated by use of precursors that have been derivatized to contain favorably reactive groups. For example, a hydrogel of this type could be assembled using a first precursor derivatized with a particular reactive moiety and a second precursor derivatized with or comprising a second moiety that can preferentially react with the first moiety on the first precursor. Likewise, other such hydrogels could be generated using such reactive pairs wherein the two moieties that react to form the bond are each conjugated to the same or a different type of polymer. For example, the pairs can be antibody-antigen pairs or avidin-biotin (e.g. streptavidin-biotin).

In other embodiments a hydrogel delivery vehicle need not be a self-assembling matrix. For example, in other embodiments a hydrogel matrix for use in vivo can be administered to a patient according to a suitable administration method (e.g., percutaneously) following assembly of the hydrogel. In other embodiments of the invention, the disclosed systems can be utilized in ex vivo applications, for example in tissue engineering applications as discussed above, and as such, a hydrogel matrix need not be a self-assembling matrix.

Delivery vehicles can include a combination of one or more delivery vehicles. For instance, a hydrogel delivery vehicle can be combined with a patch, a stent, a perforated balloon, a vascular graft, or any other suitable device, for delivery of the disclosed agents to tissue.

Delivery vehicles can also include vascular grafts. For example, an allograft, xenograft or autologous graft can be associated with one or more elastogenic cues as herein described prior to implantation. For example, a vascular graft can be coated or tethered with one or more elastogenic cues as herein described. In another embodiment, a vascular graft can be associated with a hydrogel delivery vehicle or a non-hydrogel polymeric delivery vehicle such as those described above that has in turn been loaded with an elastogenic compound. During implantation, the vascular graft can be located in association with the targeted tissue, and thus serve to deliver the elastogenic cue to the tissue.

In another embodiment, one or more elastogenic cues can be provided in pharmaceutically acceptable formulations using formulation methods known to those of ordinary skill in the art. These formulations can generally be administered by standard routes. For example, the formulations may be administered via direct injection of the formulation to the targeted tissue. In other embodiments, however, the formulations may be administered indirectly to the targeted tissue.

Elastogenic cues can be delivered intravenously in a systemic delivery protocol. For example, osmotic mini-pumps may be used to provide controlled delivery of high concentrations of the elastogenic cues through cannulae to a targeted site, such as directly into a targeted blood vessel. In situ polymerizable hydrogels, as discussed above, are another example of a delivery vehicle that can be utilized in such a delivery protocol, for instance in an intravenous delivery directly to targeted cannulae. Once delivered to the targeted blood vessel by any suitable method as is accepted in the art, elastogenic cues can contact the vessel wall and encourage the growth and development of elastogenic tissue of the vessel.

Compositions of the present invention can include additional agents, in addition to one or more elastogenic cues. Such agents can be active agents, providing direct benefit to the tissue in addition to those provided by the elastogenic cues, or may be supporting agents, improving delivery, compatibility, or reactivity of other agents in the composition.

One or more elastogenic cues can be combined with any of a number of possible lipid-lowering medications so as to prevent the development of calcified lipid deposits or arteriosclerosis plaques that can often be found in conjunction with damaged vasculature.

A composition can include one or more buffers as are generally known in the art. For example, a composition can be developed so as to have a pH from about 4.0 to about 9.0 and may be formulated with inclusion of a biocompatible buffer such as distilled water, saline, phosphate buffers, borate buffers, HEPES, PIPES, and MOPSO. In one embodiment, a composition may be formulated to have a pH of between about 5.5 and about 7.4.

Compositions for parenteral delivery, e.g., via injection, can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, a composition can contain minor amounts of auxiliary substances such as wetting or emulsifying agents, pH buffering agents and the like that can enhance the effectiveness of an elastogenic cue. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

When an effective amount of elastogenic cues are administered by intravenous or subcutaneous injection, the compositions can generally be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection can contain, in addition to the one or more elastogenic cues, an isotonic vehicle such as Sodium Chloride Injection, Ringer's Injection, Dextrose Injection, Dextrose and Sodium Chloride Injection, Lactated Ringer's Injection, or other vehicle as known in the art. A composition may also contain stabilizers, preservatives, antioxidants, or other additives known to those of skill in the art.

The dosage of the elastogenic cues can depend on the disease state or particular condition being treated and other clinical factors such as weight and condition of the human or animal and the route of administration of the compound. The disclosed treatment agents can be administered between several times per day to a single treatment protocol. Optionally, treatment agents could be delivered according to the disclosed process either acutely, during a one-time intervention, or chronically, for instance using multiple administrations or optionally a single administration of a timed or sustained releases system. It is to be understood that the present invention has application for both human and veterinary use. The methods of the present invention contemplate single as well as multiple administrations, given either simultaneously or over an extended period of time. In addition, the disclosed treatment agents can be administered in conjunction with other forms of therapy, e.g., surgical endovascular stent graft repair or replacement of an excessively damaged area of vasculature.

Prolonged absorption of an injectable pharmaceutical form may be brought about by the inclusion of agents, such as aluminum monostearate and gelatin, which can delay absorption. For example, injectable depot forms can be made by forming microencapsule matrices including elastogenic cues loaded in a matrix formed of biodegradable polymers such as polylactide-polyglycolide, poly(orthoesters) and poly(anhydrides). Depending upon the ratio of therapeutic agent to polymer and the nature of the particular polymer employed, the rate of drug release can be controlled. Depot injectable formulations can also be prepared by entrapping the therapeutic agents in liposomes or microemulsions, which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The invention may be more clearly understood with reference to the Examples set forth below.

EXAMPLES

Testing Methods

For the quantification of band intensities, bands stained with Alcian Blue as per established protocols were imaged under trans-white light in a Chemi-Imager IS 4400 system (Alpha Innotech, San Leandro, Calif.), and analyzed using system software (Alpha Ease FC). The relative oligomer band intensities were calculated from the ratio of the intensity of each band to that of the 4-mer loaded at 5 ng/lane, and used as a staining control. The reproducibility tests for staining were performed with n=3 samples/condition applied within the same gel (intra-assay variation) and loaded on three separate gels (inter-assay variation).

A Fastin assay (Accurate Scientific and Chemical Corporation, Westbury, N.Y.) was used to quantify the total amount of soluble α-elastin present as matrix-elastin (P2), and soluble tropoelastin (S1). As is necessitated by the assay, insoluble elastin was first reduced to a soluble form. The elastin pellet (P2) was dried to a constant weight, solubilized with 0.25 N oxalic acid (3 cycles, 1 h/cycle, 95° C.), and the pooled digests then filtered in microcentrifuge tubes fitted with low molecular weight cut-off membranes (10,000 Da). The insufficiently crosslinked, soluble elastin fraction retained in the oxalic acid-free fraction (S3) and in the water-reconstituted hydrolysate (S2) were also quantified using the Fastin assay. Spent fractions of media were pooled at bi-weekly intervals over the 3 weeks culture, lyophilized and processed for tropoelastin using the Fastin assay, performed as described previously (Joddar, et al. *Biomaterials*. 2006; 27(15): 2994-3004). The assayed weight of insoluble elastin was compared to that determined by weighing the dry elastin pellet (P2), to affirm low/no loss of elastin material during matrix processing.

For PAGE, HA digest samples in the digestion buffer were mixed with one-fifth volume of 2M sucrose in Tris-borate-EDTA buffer (Sigma) and 2-µl well mixed aliquots applied directly to 16% w/v, Novex Tris-Glycine gels (Invitrogen, Carlsbad, Calif.), and electrophoresed (125 V, 2.5 h, 4° C.). Bromophenol blue (BPB; 0.005% w/v in Tris-borate-EDTA buffer) containing 0.3M sucrose (Sigma) was used as a tracking dye, in one well (no sample). The reservoir buffer used was Tris-borate-EDTA. The identity of generated bands was confirmed by comparing with an HA oligomer standard ladder (nano HA ladder; Associates of Cape Cod, East Falmouth, Mass.).

MALDI-TOF MS analyses of HA oligomers were performed on a Voyager-DE STR Biospectrometry Workstation (Applied Biosystems, Foster City, Calif.) in a linear mode. The spectrometer was calibrated using a mixture of angiotensin I (MH+=1296.7 Da) at a concentration of 2.0 pmol/µl, adrenocorticotrophic hormone amino acids (18-39 clip, MH+=2466.72 Da) at a concentration of 1.5 pmol/µl, (1-17 clip, MH+=2094.46 Da) at a concentration of 2.0 pmol/µl, (7-38 clip, MH+=3660.19 Da) at a concentration of 3.0 pmol/µl and bovine insulin (MH+=5734.59 Da) at a concentration of 3.5 pmol/µl in an α-cyano-4-hydroxycinnamic acid matrix (PerSeptive Biosystems Inc., Framingham, Mass.) and scanned over a mass range of 0-50,000 Da. The MALDI matrix used for sample analysis was α-cyano-4-hydroxycinnamic acid (8 mg/ml in 50% v/v acetonitrile, 0.3% v/v trifluoroacetic acid). Samples (2 µl) containing equal volumes of matrix and sample solution were coated and air-dried onto a stainless steel target. Positive spectra were recorded in a linear mode using the minimum laser energy required to give an observable signal (~10:1 signal:noise). All sample digests (n=3/condition) were each analyzed in at least triplicate using MALDI-TOF. The commercial HA oligomer preparations were also similarly analyzed for fragment size distribution (n=3/condition).

At 1 and 21 days of culture, the DNA content of the cell layers was measured to determine the proliferation of SMCs and to normalize the measured amounts of synthesized matrix (elastin, collagen). The fluorometric DNA assay, described previously by Labarca and Paigen (Labarca C, Paigen K. A simple, rapid, and sensitive DNA assay procedure. Anal Biochem. 1980; 102:344-52), was performed on cell layers processed as described previously (Joddar B, Ramamurthi A. Fragment size- and dose-specific effects of hyaluronan on matrix synthesis by vascular smooth muscle cells. Biomaterials. 2006; 27(15): 2994-3004). Actual cell counts were then calculated on the basis of an estimated 6 pg DNA/cell.

A Hydroxy-proline (OH-Pro) assay was used to estimate the collagen content within test and control cell layers, as described previously (H. Stegeman and K. Stalder, Determination of hydroxyproline, *Clin Chim Acta* 18 (1967), pp. 267-273). For the assay, 4 ml homogenized, cell suspensions in d.d. water were pelleted by centrifugation (10,000 g, 10 min; P1), then dried to a constant weight and digested with 1 ml of 0.1 N NaOH (1 h, 98° C.). The digestate was then centrifuged to isolate a mass of insoluble, crosslinked elastin (P2). The supernatant (S1) containing solubilized collagen and immature matrix elastin was acid-neutralized with 12 N HCl, divided into two equal volumetric halves and heated on a heating block (110° C., 16 h). The measured amounts of OH-Pro were corrected to account for the 4% w/w of OH-Pro contained in solubilized elastin present in the reconstituted sample (S2). Finally, the total amount of matrix-derived collagen was calculated on the basis of the 13.2% OH-Pro content of collagen.

SDS-PAGE and Western Blot were performed to confirm the observed biochemical trends for synthesis of soluble tropoelastin. Briefly, the aliquots of spent medium removed and pooled at bi-weekly intervals over the 21-day culture period, were lyophilized, assayed for protein content using a DC protein assay kit (Biorad Corporation, Hercules, Calif.), and subjected to SDS-PAGE and Western Blot. Optimized sample amounts (20 µg) were appropriately mixed and boiled (100° C., 5 min) with a loading buffer (2% w/v Sodium Dodecyl Sulfate (SDS), 62 mM Trizma base, 10% v/v Glycerol, 600 mM dithiothreitol), flash-spun in an ultracentrifuge (500 g, 2 min) and loaded under reduced conditions onto 10% w/v polyacrylamide gels (Novex Tris-Glycine gels, Invitrogen Corporation, Carlsbad, Calif.), with prestained protein standards ranging between 10-190 kDa (Benchmark Pre-stained Protein Ladder, Invitrogen) and western blot standards ranging between 20-220 kDa (MagicMark XP Western Protein Standards, Invitrogen). Electrophoresis was performed in an Xcell SureLock Mini-Cell (Invitrogen) for 2 hours at 125V until the dye front touched the bottom of the gel. Following electrophoresis, the protein bands were transferred onto a PVDF pre-wetted membrane, developed, imaged using trans-white light, and quantified using the Alpha Innotech imaging software (Alpha Ease FC; Chemi-imager 4400) as described previously. Individual band intensities were then normalized to the corresponding DNA content of the same samples and were finally compared as band intensity on a per ng of DNA basis.

Desmosine content of the cell-matrix layers was determined in expectation that it would correlate with the amounts of crosslinked elastin and serve as an indirect confirmation of the earlier observed biochemical trends, with regard to synthesis of matrix elastin. To assess desmosine content, compounded test and control cell pellets were digested with collagenase type VII (Sigma; 12 h, 37° C.) and re-centrifuged (3000 g, 10 min, 4° C.) to obtain a supernatant (SI) and a pellet. This pellet was digested with pancreatic porcine elastase type III (Sigma; 12 h, 37° C.) to obtain a soluble peptide fraction (SII). Fractions SI and SII were pooled together, acid-hydrolyzed with 6 N HCl (110° C., 16 h), dried under a stream of inert N2, re-constituted in water and the desmosine content determined by ELISA as previously done.

Immunofluorescence was used to confirm the presence of elastin and collagen within cell layers. Cells cultured in the presence of HA oligomers (pure 4-mers and mixtures, 2 µg/ml) and their absence (controls) were rinsed briefly in PBS, fixed in 4% v/v paraformaldehyde (10 min, 4° C.), and labeled with Alexa 448 Phalloidin, a fluorescent probe for smooth muscle cell actin (1:20 dilution; 20 min, 25° C.).

Elastin and collagen were detected with rabbit anti-rat elastin or collagen primary antibodies and visualized with donkey anti-rabbit Cy-5-conjugated probes (Chemicon). Cell nuclei were labeled with the nuclear stain 4', 6-diamino-2-phenylindole dihydrochloride (DAPI; Molecular Probes) dissolved in PBS. Elastin and collagen present in fixed specimens of rat aortae were stained as positive controls for the antibodies. Negative control specimens (both cell layer- and tissue-sections) were not treated with the primary antibody against elastin or collagen.

Transmission Electron Microscopy (TEM) was used to selectively compare the distribution and ultrastructure of matrix elastin between cell layers cultured with or without exogenous bolus of HA oligomers, pure or their mixtures (2 µg/ml). For TEM, the adhered cell layers were fixed in 2.5% v/v glutaraldehyde in sodium cacodylate buffer, and post-fixed in 1% v/v OsO4, then dehydrated with ethanol. These samples were then embedded in resin, sectioned longitudinally using an electric roll saw (Sears, Hoffman Estates, Ill.), and re-embedded for orientation and polymerization. Thick sections were cut using an ultramicrotome (Reichert Microscope Services, Depew, N.Y.), stained with toluidine blue, and examined under a light microscope to choose appropriate blocks for the presence of an exuberant elastin matrix layer as seen previously by us with cell cultures on crosslinked HA gels. Representative blocks were ultrasectioned into 70 nm thin sections, contrast-stained with uranyl acetate and lead citrate, and then visualized on a transmission electron microscope (JEOL USA Inc., Peabody, Mass.).

Immunogold labeling and TEM were used to detect presence of fibrillin microfibrils that would confirm non-interference of HA oligomers with normal physiological mechanism of elastin matrix deposition. Briefly, test and control cell layers were incubated with a rabbit anti-rat primary fibrillin-I antibody (20% v/v; 14 h, dark; Elastin Products Company, Owensville, Mo.), and then treated with a goat anti-rabbit IgG conjugated with gold nanoparticles (10 nm; Structure Probe, Inc., West Chester, Pa.). Cell layers were processed identical to that performed for TEM. Ultrathin (70 nm) sections were prepared, counter-stained as described in above and visualized. Cell layers untreated with the primary antibody served as negative controls.

To determine LOX functional activity, spent culture medium pooled at day 21 of a culture was assayed using a fluorometric assay based on generation of $H_2O_2$ when LOX acts on a synthetic substrate. $H_2O_2$ was detected using an Amplex® red kit (Molecular Probes, OR,). The fluorescence intensities were recorded with excitation and emission wavelengths at 560 nm and 590 nm, respectively Example 1

Two different HA oligomer preparations including HA oligomers at a concentration of 0.2 mg/ml were tested for their effect on elastin matrix synthesis. One was a commercially procured, highly pure (99% w/w) 4-mer (Hyalose, Okla. city, OK) and the other, an enzymatic digest of long-chain HA containing HA 4-mers as a predominant component, among other HA oligomers. FIG. 2 is a flow diagram illustrating the biochemical analysis carried out in the Example. These HA oligomer preparations were compared to a control (no HA) as well as various concentrations of HA polymers including high molecular weight HA polymers (HMW–$M_n$~$2\times10^6$ Da), low molecular weight HA polymers (LMW–$M_n$~$2\times10^5$ Da), and very low molecular weight polymers (VLMW–$M_n$~$2\times10^4$ Da).

Preparation and Characterization of HA Oligosaccharide Mixtures

To prepare HA oligomer mixtures, HMW HA (MW~$2\times10^6$ Da; Genzyme Biosurgery, Cambridge, Mass.) was digested with bovine t. hyaluronidase (Sigma-Aldrich, St. Louis, Mo.), in doses ranging between 40-160 U of enzyme/mg HA over time periods between 20 minutes and 48 hours, at 37° C. (n=10/condition). HA oligomers in the digestate were subsequently analyzed by PAGE (Polyacrylamide Gel Electrophoresis) and the size of the generated series of bands calculated based upon their mobility in the electrophoresis gel relative to a ladder of known standards. Simultaneously, the HA digests were also analyzed by MALDI-TOF (Matrix Assisted Laser Desorption/Ionization Spectroscopy Time-Of-Flight Analysis) to determine the HA fragment size distribution and relative abundance within the digests (n=10/sample). The amounts of HMW HA and t. hyaluronidase enzyme used, and the time of enzymatic digestion were optimized based upon the predominance of the 4-mer in the digestate, assessed by PAGE and MALDI-TOF. In the final optimized protocol, HA (20 mg) was enzymatically digested (3.6 mg HAase, 451 U/mg) in 4 ml of digest buffer (150 mM NaCl, 100 mM CH3COONa, 1 mM Na2-EDTA, pH 5.0) at 37° C. for 18 hours. The enzyme activity was terminated by boiling the mixture in a water bath for 5 minutes following digestion. The mixture was dialyzed against water (12 hours) and frozen until use at −20° C.

Preparation of HA-Oligomer Bolus

Fresh, filtered solutions of lyophilized HA oligomers, dissolved in serum-free DMEM: F12 (Invitrogen, Grand Island, N.Y.; 48 hour, 4° C.) were added to cell cultures at a stock concentration of 10 µg/5 ml (1 ml stock per 4 ml serum-rich medium). The added concentration of the oligomers was selected such as to lie within a range of between about 0.2 µg/ml and about 200 µg/ml, and also lie within a dose range of between about 1 and about 100 µg/ml, shown to be effective in influencing responses of other cell types.

Cell Culture

Adult rat SMCs (RASMCs, Passage 6-8; Cell Applications, San Diego, Calif.) were seeded onto 6-well tissue culture plates (Becton Dickinson Labware, Franklin Lakes, N.J.; A=10 cm$^2$) at a count of $10^5$ cells/10 cm$^2$. After overnight culture, the spent medium from atop cell layers was replaced with HA-solubilized medium (test cell layers) and serum-rich medium only (controls). All experimental trials and controls were performed in triplicate. The spent medium containing dissolved HA oligomers, was replaced twice weekly, pooled and analyzed at the end of the 21-day culture period. Cells were also seeded onto 4-well sterile chamber slides (Nalgene Nunc International, Rochester, N.Y.) at a count of $10^4$ cells/2.4 cm$^2$ for a period of 21 days for immunodetection of elastin and collagen in the matrix.

HA oligosaccharides present in the HA digestates appeared as bands entrapped within the PAGE gel, and up took Alcian blue within 15 minutes of gel staining. Only sporadic intra-assay and inter-assay variations were observed in intensity of HA oligosaccharide bands. MALDI-TOF MS analysis consistently yielded the same oligomer size ranges and oligomer peaks observed under specified conditions of HA digestion.

Enzymatic Digestion of HA (20 min, 20 mg of HA, 40 U of enzyme/mg HA) yielded a range of HA fragments that were visualized, as Alcian blue-stained bands on a polyacrylamide gel and identified as 4-22 mers. Based on these outcomes, enzyme amounts and the digestion times were sequentially varied to finally obtain HA oligomer products of sizes within a narrow range (4-8 mers). The digestion time was varied up to a maximum of 48 hours and the amount of enzyme used for digestion was maximized up to 160 U of enzyme/mg HA to generate the desired oligomer size range. Finally, a narrow size-range of oligomers (4-8 mers) was obtained by digestion of HMW HA (20 mg) with 81 U of enzyme/mg HA for 18 hours. No variations in band distribution and respective band intensities were observed when triplicate samples were run within the same gels (intra-gel variation) and on three separate gels (inter-gel variation).

MALDI-TOF spectra for replicate aliquots of HA digests (20 mg HA; 81 U of enzyme/mg HA, 18 h) consistently yielded a narrow range of HA oligosaccharides (4-8 mers, MH+=657-2172 Da) confirming the PAGE results. The predominant peak % intensity corresponded to HA oligomer of sizes approximately in the range of MH+=657 Da, i.e. in the size range of the 4-mer. Tested control aliquots (digest buffer with no HA) yielded several peaks (170-192 Da), all of much lower intensity and of smaller sizes than the desired peaks in the oligosaccharide size range.

MALDI-TOF was also used to compare the % peak intensity of HA 4-mer peaks generated in digests of both commercial preparations and in-house prepared oligomer mixtures (2 µg HA/ml). The intensity of the lone peak corresponding to the O-mer in the commercial preparation (2 µg/ml) was considered 100% w/v pure for comparison. The % peak intensity for the 4-mer component of the in-house prepared oligomer mixture was 75±0.4% w/w.

At day 1, actual cell numbers attached represented 75±0.4% and 125±1% of the theoretical seeding number ($10^5/10$ $cm^2$) for pure 4-mers and controls, and the mixture-supplemented cultures, and their controls, respectively. Control cells proliferated 1.8±0.1 times the original seeded number, at 21 days of culture (n=3). Cells supplemented with pure HA 4-mers or HA oligomer mixtures showed proliferation levels similar to controls (1.66±0.05 and 1.71±0.16 times number at 1 day; p=0.15, p=0.14 for pure and mixture vs. controls respectively; n=3/case/time point). Differences in proliferation ratios between cell layers supplemented with the pure 4-mer and the HA oligomer mixtures were statistically insignificant (p=0.35 at 21 days).

Figure 3:
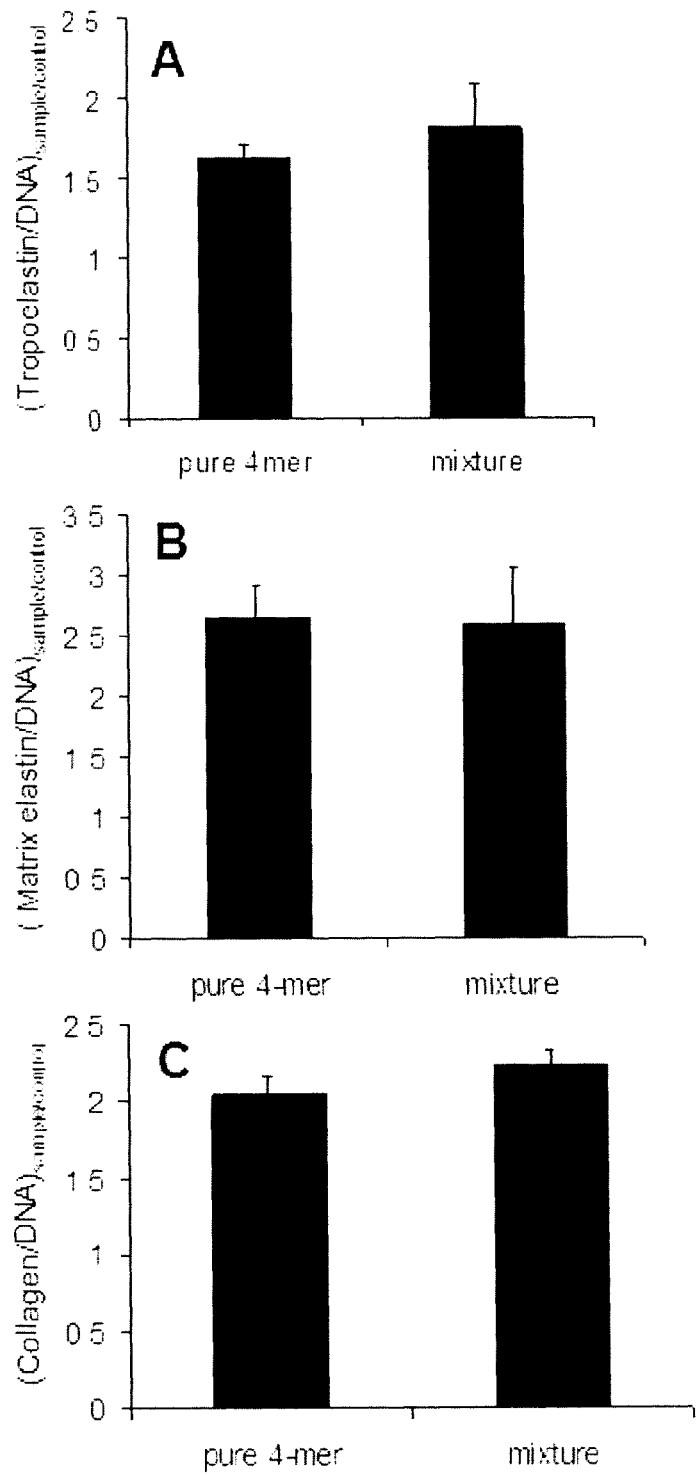
FIGS. 3A-3C illustrate the effects of exogenous HA 4-mer and oligomer mixtures containing HA 4mers included in an SMC culture on extracellular matrix (ECM) protein synthesis including tropoelastin synthesis (FIG. 3A), matrix elastin synthesis (FIG. 3B), and collagen synthesis (FIG. 3C)

The measured tropoelastin amounts (ng) were normalized to the average DNA content (ng). In general, cell layers supplemented with pure HA 4-mer, and HA oligomer mixtures showed 1.63±0.06 and 1.82±0.26 times the tropoelastin output relative to their respective control cultures (161,531±6,901 (ng/ng), and 112,871±16,113 (ng/ng) respectively; n=3) (FIGS. 1 and 3A and FIG. 2 for methods). There were no statistical differences in tropoelastin synthesis between cultures supplemented with the pure HA 4-mer or the oligomer mixture (p=0.14; n=3/case).

Elastin synthesized and incorporated into the extracellular matrix was measured as a sum of two components, namely, a highly crosslinked, alkali-insoluble elastin pellet, and a crosslinked, but alkali-soluble fraction. In general, the total DNA-normalized output of matrix elastin for HA-oligomer supplemented cell cultures was significantly higher than that of control (non HA) cultures. In the presence of HA pure 4-mers, DNA normalized matrix elastin output was 2.7±0.3 times that produced by controls (858±25 ng/ng). Similarly the DNA normalized matrix elastin output by cells cultured with the HA oligomer mixture was 2.6±0.5 times that produced in their controls (703±42 ng/ng; FIG. 3B, and FIG. 2 for methods). Differences between the test cultures (pure HA 4-mers vs. oligomer mixtures) were deemed statistically insignificant (p=0.42; n=3).

Figure 4:
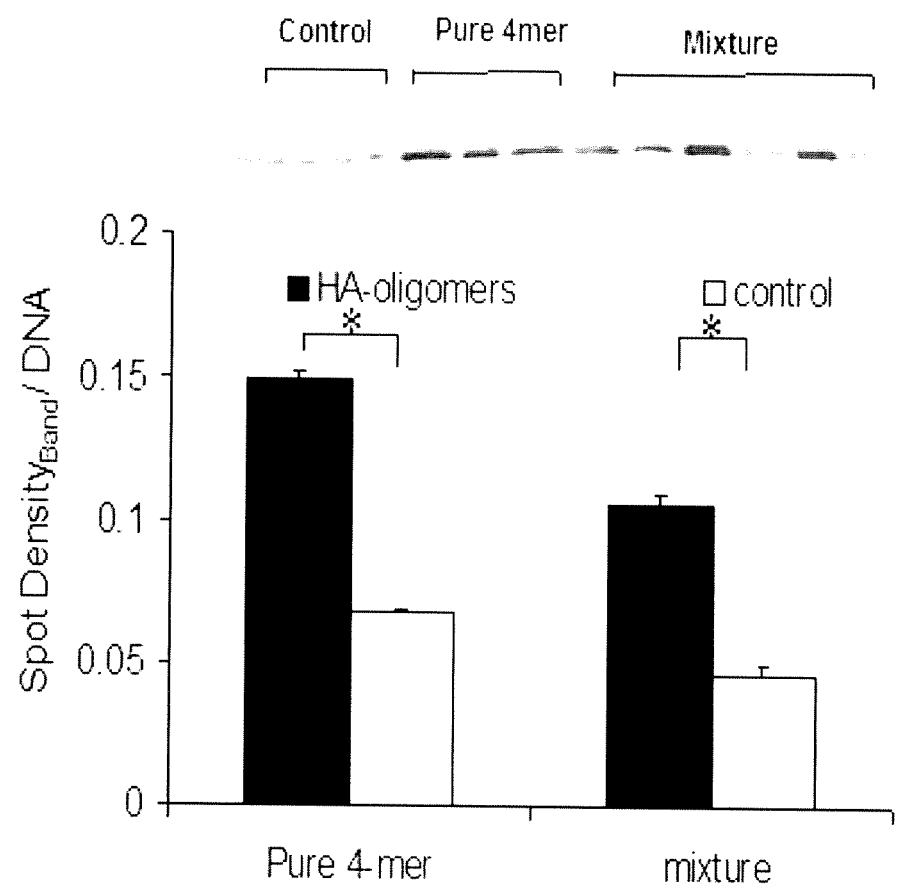
FIG. 4 illustrates the effects of exogenous HA 4-mer and oligomer-mixtures included in SMC cultures on tropoelastin production.

The measured collagen amounts were normalized to DNA content of their respective source cell layers (ng/ng). In general, exogenous HA-oligomers induced significantly more collagen synthesis compared to controls (no HA) cultures. Collagen production by cell layers supplemented with pure HA 4-mers, and HA oligomer mixtures were 2.0±0.1, and 2.2±0.1 times that produced in their respective controls (336±22, 209±5 ng/ng; FIG. 3C, and FIG. 2 for methods). The differences in these ratios between cell layers supplemented with the pure 4-mers and HA oligomer mixtures showed no significant differences (p=0.04; n=3/case). Band intensities (pixel intensity) of tropoelastin from stained blots were normalized to corresponding DNA amounts in the source cell layers (ng). Normalized band intensities for HA-oligomer supplemented cell cultures (0.15±0 for pure HA 4-mer, and 0.11±0 for oligomer mixtures; n=3/case) were greater than that obtained for their controls (0.07±0, and 0.05±0; n=3) (FIG. 4).

Desmosine amounts measured in test cell layers were normalized to corresponding DNA amounts (ng/ng), and further a similar ratio obtained for the non-HA controls. Cells cultured with HA-oligomers showed greater amounts of desmosine synthesis (FIG. 1, 4.76±0.10 for pure HA 4-mer, and 4.57±0.11 for the oligomer mixtures) in comparison to their respective controls.

Immunofluorescence studies confirmed presence of elastin in the matrix of 21 day-old test and control cell layers. However the density of elastin was much greater in the HA-oligomer supplemented cell layers than in controls. In addition, the HA-supplemented cultures exhibited a much higher degree of organization into fibrous networks than in control cultures, which rather exhibited more random clumpy elastin. Collagen was also more abundantly distributed in HA-oligomer supplemented cultures in comparison to controls and more uniformly distributed unlike the latter. Aortal elastin and collagen treated with the respective elastin and collagen primary antibodies and secondary probes tested positive for elastin and collagen respectively. Cell layers and aortae not treated with the primary antibody to rat elastin and collagen (negative controls) confirmed the absence of non-specific binding of the Cy-5 fluorophore.

Transmission electron micrographs of cell layers cultured with HA-oligomers (pure 4-mers and mixtures) for 21 days showed multiple layers of elongated, aggregating elastin fibrils and clumps uniformly sandwiched between alternating cell layers. No difference was observed in the density and appearance of the elastin fibers in between HA pure 4-mer samples and oligomer mixture (n=30/case) treated samples. Control cell layers at 21 days could be distinguished from sample cell layers due to the presence of far fewer elastin fibrils and a large number of amorphous elastin clumps, surrounded by deeply staining microtubules, typical of elastic fiber formation. Elastin fibrils appeared to laterally aggregate, symbolizing formation of thicker elastin fibers. Collagen fibers, characterized by their characteristic light and dark banding patterns were also seen in all cases, but were not as numerously distributed as was elastin. Both control and test cell layers tested positive for presence of fibrillin, which appeared in longitudinal and cross-sections as darkly stained microfibrillar networks at the periphery of elastin fiber bundles. Such darkly stained fibrils were not visible in non-immunogold labeled cell layers. The average length of the fibrillin strands was 72±16 nm, comparable to that specified in literature (~67 nm).

Though HA has been shown to primarily interact with CD44 and RHAMM cell surface receptors an SDS-PAGE/Western Blot were performed to determine if HA oligomers indirectly influence elastogenesis and elastin stability through their modulation of the activity of the elastin-laminin receptor (ELR). For ELR immunoblotting, whole cell lysates (n=3 per group) were prepared using RIPA buffer (50 mM Tris, 150 mM NaCl, 1 mM EDTA, 1% v/v Triton X-100, 1% v/v sodium deoxycholate, and 0.1% v/v SDS, pH 7.4) and 10 µl/ml protease inhibitor composition (Sigma, St. Louis, Mo.). Cell layers which received HA 4-mers and in-house mixtures (2 mg/ml) and no HA oligomers (controls) were harvested, sonicated in RIPA buffer, and incubated overnight at 4° C. Samples were normalized to protein content by bicinchoninic acid assay (BCA Protein assay kit, Pierce, Rockford, Ill.) and 20 µg of protein for each sample was loaded under reducing conditions, onto wells in a 10% w/v polyacrylamide gels (Novex Tris-Glycine gels, Invitrogen Corporation, Carlsbad, Calif.), with prestained protein standards ranging between 10-190 kDa (Benchmark Pre-stained Protein Ladder, Invitrogen). Electrophoresis was carried out in a Xcell SureLock Mini-Cell (2 h, 125V) until the dye front touched the bottom of the gel. After electrophoresis, the proteins were transferred to Immobilon-P transfer membranes (Millipore, Bedford, Mass.), blocked in 2% w/v non-fat dried milk (1 h, 23° C.), and then probed with an anti-67 kDa laminin receptor primary antibody (Abcam, Cambridge, Mass.; 1:500 dilution in PBS) overnight at 4° C. The ELR protein at 67 kDa (cytoplasmic precursor of 67 kDa protein) was detected using Western Breeze (Chromogenic anti-rabbit western blot immunodetection kit, Invitrogen), imaged using a Chemi-Imager IS 4400 system (Alpha Innotech, San Leandro, Calif.), and bands visualized and quantified using associated software.

Figure 5:
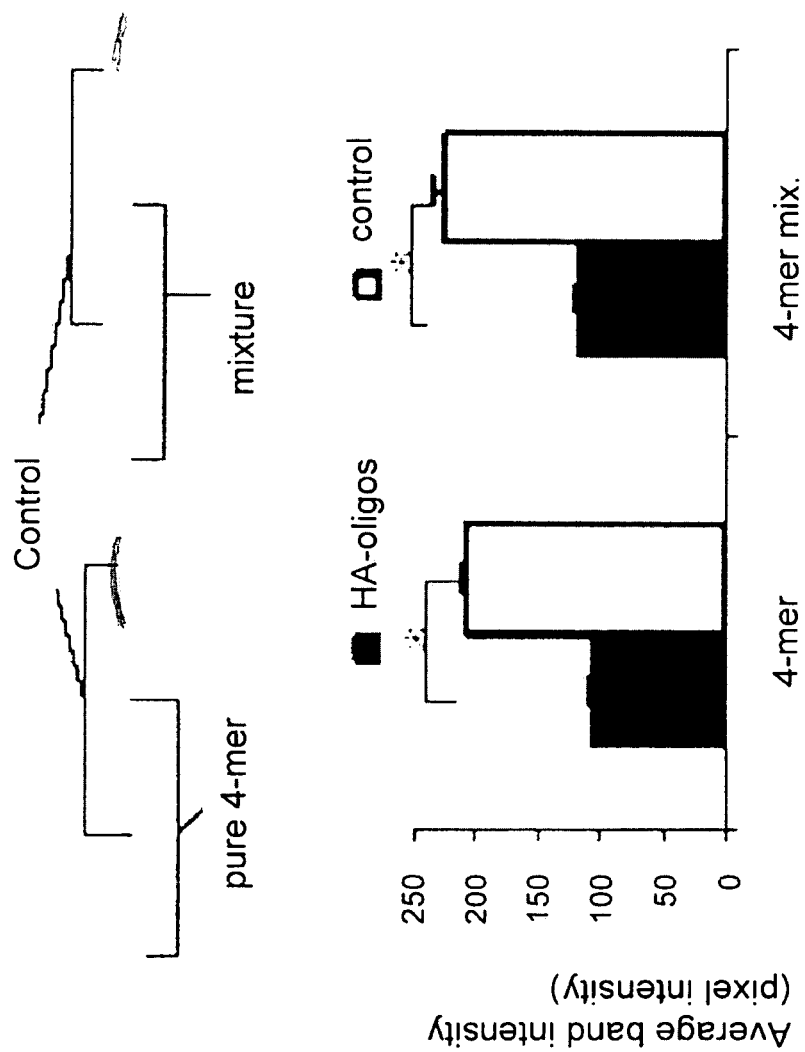
FIG. 5 illustrates the effect of HA oligomers in suppression of elastin-laminin receptor (ELR) activity.

The band intensity corresponding to ELR activity was lower in HA-oligomer supplemented cultures relative to controls. FIG. 5 shows the average band intensities, proportional to ELR activity in cell layers, for test HA-oligomer-supplemented cultures, and non-HA controls. ELR activity was suppressed by 52±1% in test cultures compared to controls.

Example 2

Enzymatic degradation studies were performed to compare the impact of HA oligomer exposure and their mode of delivery on elastin matrix quality, particularly their resistance to enzymatic breakdown. Elastin matrices isolated by alkali digestion of aortae explanted from adult Sprague-Dawley rats served as additional controls for these studies. Briefly, adult rat aortal segments were removed from euthanized rats, from arch to the celiac axis, under sterile conditions, and spliced lengthwise in petri dishes containing cold phosphate-buffered saline (PBS) containing 2 mM $Ca^{2+}$. These spliced sections were then transferred to a dish containing 1-2 ml of collagenase (2 mg/ml; Worthington, Lakewood, N.J.) and incubated for 10 minutes at 37° C. DMEM:F12 media was then added to these collagenase treated samples and mixed well with gentle pipetting. Isolated aortal segments were further chopped crosswise into 0.5-m long pieces and transferred using fine needles onto sterile petri dishes and stored in PBS at 4° C. until further use. Cell layers were scraped off the culture wells, pelleted by centrifugation (2000 g, 15 min), and stored at −20° C. in PBS until further use (n=9/case).

HA tetramers as described above in Example 1 were tethered onto 4-well glass chamber slides (Nalge Nunc International, Naperville, Ill.). The chamber slides were incubated in 1 M NaOH for 1 hour to de-protonate the exposed hydroxyl groups and render the glass surface uniformly reactive. The glass surface was rinsed with DI water and 95% v/v ethanol (Sigma, St Louis, Mo.), and then activated by incorporation of aminosilanes. A 3% v/v solution of 3-aminopropyl-trimethoxysilane (APTMS; Fluka Chemical Corp., Milwaukee, Wis.) in 95% v/v ethanol was prepared and the silane was allowed to convert into silanol over 5 minutes. A 1-ml aliquot of the solution was then reacted with the glass slide (30 min, 23° C.) with shaking. The slides were then briefly rinsed in 100% v/v ethanol (Sigma), dried under a steady stream of argon gas, and finally heated in an oven (1 hr, 115° C.), rinsed three times with 95% v/v ethanol, and dried again under argon gas.

Immobilized amines were covalently reacted with the carboxyl groups present on HA, using a carbodiimide reaction. Briefly, an aqueous HA solution (3 mg/ml) was prepared with 200 mM 1-Ethyl-3-[3-dimethylaminopropyl]carbodiimide hydrochloride (EDC; Pierce Biotechnology Inc., Rockford, Ill.) and 100 mM N-hydroxysuccinimide (NHS; Pierce Biotechnology Inc.). A 1 ml aliquot of this solution was applied to each well and allowed to react for 16 hours with continuous agitation on a shaker. The slides were then soaked in DI water for 2 hours to remove unbound HA, and finally air-dried under argon gas.

Adult rat SMCs (RASMCs, Passage 6-8; Cell Applications, San Diego, Calif.) were seeded onto 6-well tissue culture plates (Becton Dickinson Labware, Franklin Lakes, N.J.; A=10 $cm^2$) at a count of $10^5$ cells/10 $cm^2$. Plates included those prepared with tethered tetramers as described above as well as untreated plates. After overnight culture, the spent medium from atop cell layers was replaced with HA-solubilized medium (exogenous HA tetramer cell layers) or serum-rich medium only (controls and surface-tethered HA tetramers). All experimental trials and controls were performed in triplicate.

Harvested cell layers were processed as described above to obtain pellets of alkali-insoluble elastin. The aortal tissues were separately rinsed in cold saline to remove fat and adherent tissues, sectioned into smaller pieces, and stored at −20° C. in PBS until further use (n=9/case). Specimens were suspended in 100 mM NaOH and incubated at 37° C. for 5 hours on a shaker at 180 rpm to extract all cellular material, non-collagenous components, and some of the collagen, leaving the insoluble elastin matrix intact. These samples were then rinsed in d.d. water and incubated with collagenase II (0.5 units/mg of wet tissue; Worthington Biochemical Corporation, Lakewood, N.J.) in 50 mM TRIS buffer, 10 mM $CaCl_2$, pH 8.0 on a shaker at 180 rpm (37° C., 2 h). This step completely removed residual collagen, leaving behind pure elastin. These samples were lyophilized, their dry weights recorded, and incubated with 1 ml of 20 units/ml of elastase (Worthington) solutions prepared in 100 mM Tris buffer, 1 mM $CaCl_2$, 0.02% $NaN_3$, pH 7.8 on a shaker at 600 rpm (37° C., up to 6 h). Residual pellets (n=9/case) were centrifuged at 2000 g for 15 min (4° C.), rinsed in d.d. water, lyophilized, weighed and the % loss of elastin calculated from dry weights of pellets before (0 h) and after (6 h) exposure to elastase, using the following equation:

$$\text{Elastin Loss} = \frac{Dryweight_{0\,h} - Dryweight_{6\,h}}{Dryweight_{0\,h}}$$

Digestate solutions were also analyzed via SDS-PAGE for soluble elastin products (n=9/case/time point). Briefly, all solutions were incubated at 95° C. for 10 min and loaded onto 10% w/v Tris-Glycine gels (Invitrogen) under reduced conditions. Elastin degradation products entrapped within the gel were visualized using silver staining with 0.1% w/v $AgNO_3$ solution (Sigma). Purified elastin (EPC) was used as a staining control. The band intensities of the elastin degradation products were quantified using Chemi-Imager IS 4400 system (Alpha lnnotech).

Figure 6:
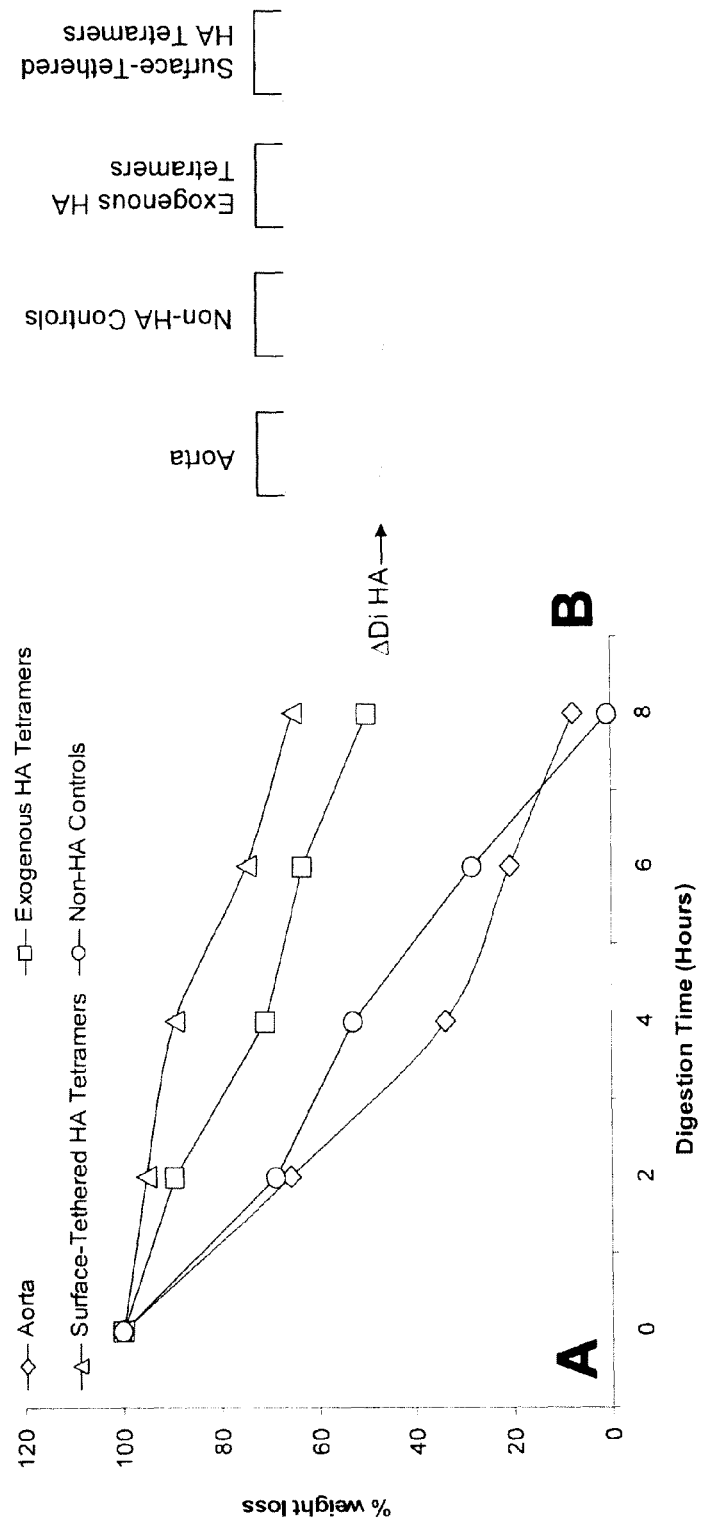
FIG. 6A illustrates the degradation rates of elastin isolated from cellular constructs cultured on matrices including HA compositions as herein described, and native elastin from aorta.
FIG. 6B illustrates the digestate from the samples of FIG. 6A following SDS-PAGE gel extraction and silver-staining.

Elastase treatment and digestion of processed aortal samples and cell pellets cultured in the presence of HA oligomers showed that the cell-pellets were relatively resistant to elastase degradation as compared to aortal sections. Thus, over an 8-hour period of enzymatic digestion, aortal samples and HA oligomer-untreated cell pellets showed a % weight losses of approximately 92% and 99% respectively (FIG. 6a). However, cell pellets cultured in the presence of surface-tethered and exogenous HA 4 mers lost only 50% and 35% of their total weight respectively (FIG. 6a). The digestate from the above aortal and pellet samples, which were run through an SDS-PAGE gel and silver-stained, showed higher band intensities for aortal samples than for cell pellets generated from cultures containing HA oligomers (FIG. 6b). This in turn indicated that the elastase enzyme created greater amounts of soluble elastin peptides from controls (aortae) than in HA-treated samples, since all other variables (e.g., digestate volume for all control and test samples was maintained at 1 ml) were kept constant.

Peptide analysis was performed using mass spectrometry, to compare masses of contained peptides (i.e., amino acid sequences) within purified elastin derived from cell layers exposed to exogenous and surface-tethered HA oligomers, or no additives (control) and to compare the quality of cultured elastin and that of native matrix elastin extracted from adult rat aorta (n=9/case for all experimental samples and control samples).

For peptide analysis, elastin synthesized by cell pellets and also present in native aorta were extracted using methods described above. Briefly both cell pellets, and defatted aortal sections were homogenized and treated with 100 mM NaOH at 37° C. for 5 hours on a shaker at 180 rpm, and then oven dried (2 h, 60° C.), weighed, alkali-insoluble elastin pellet spliced into smaller soluble elastin peptides with elastase (50:1 v/v tissue to enzyme, prepared in 1 mM Tris buffer, 37° C., 24 h). These soluble peptides were then precipitated with acetone to remove unwanted salts (PBS solution) and detergents (SDS), which could interfere with analysis, and increase the noise/signal ratio. Finally, the peptides were loaded onto a c18 trap column (Thermo Electron Corporation, Waltham, Mass.), de-salted and concentrated, loaded onto 75 μm analytical C18 RP columns (Thermo Electron Corporation), and eluted off by a gradient from 2%-70% v/v acetonitrile in the presence of 0.6% v/v heptafluorobutyric acid (HFBA). Eluting peptides were analyzed on a Thermo Finnigan LTQ mass spectrometer (Thermo Electron Corporation) using a data-dependant MSMS acquisition. Resulting data was searched against a database applying filters to identify as many peptides as possible from any given sample.

Figure 7A:
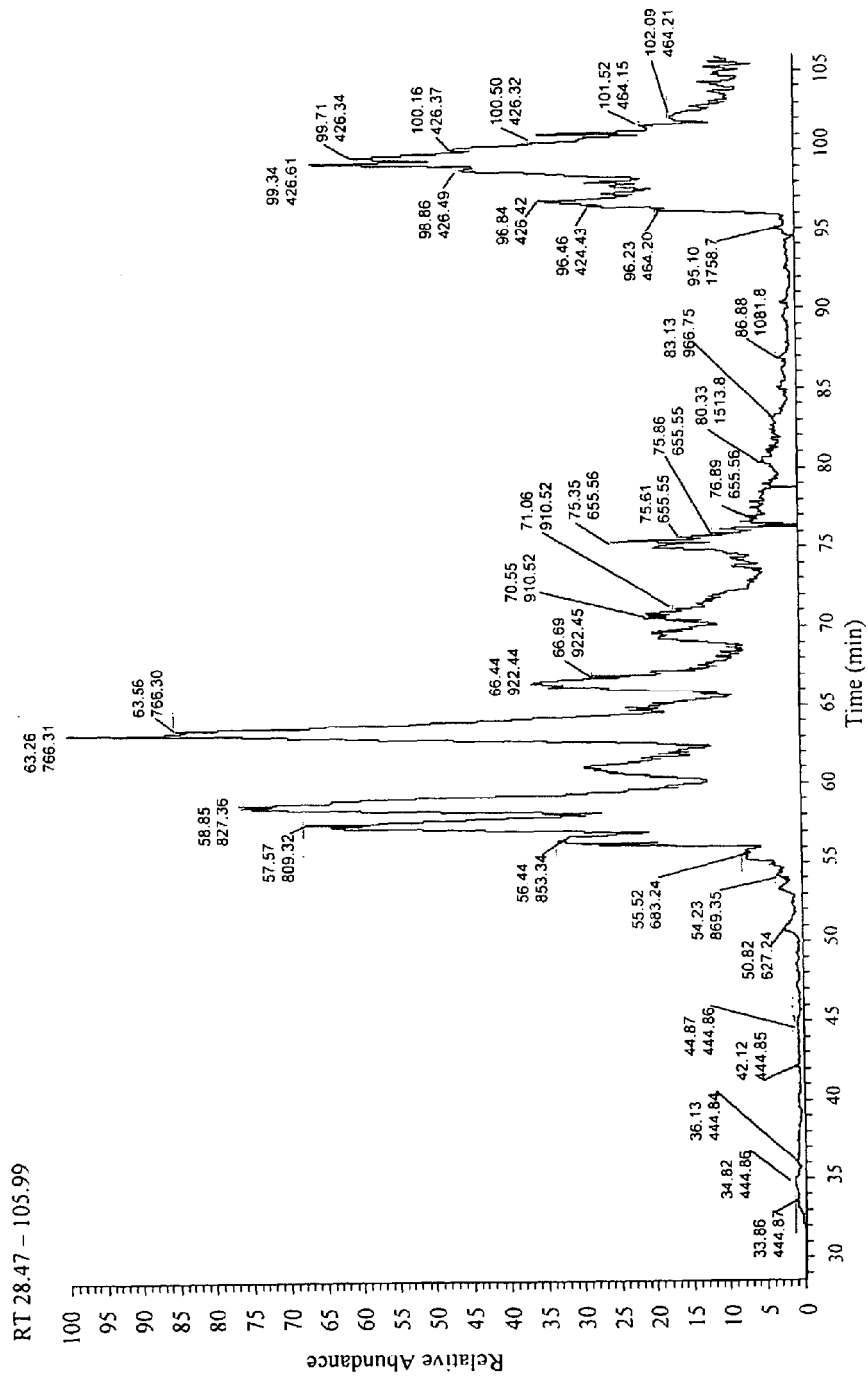
Figure 7B:
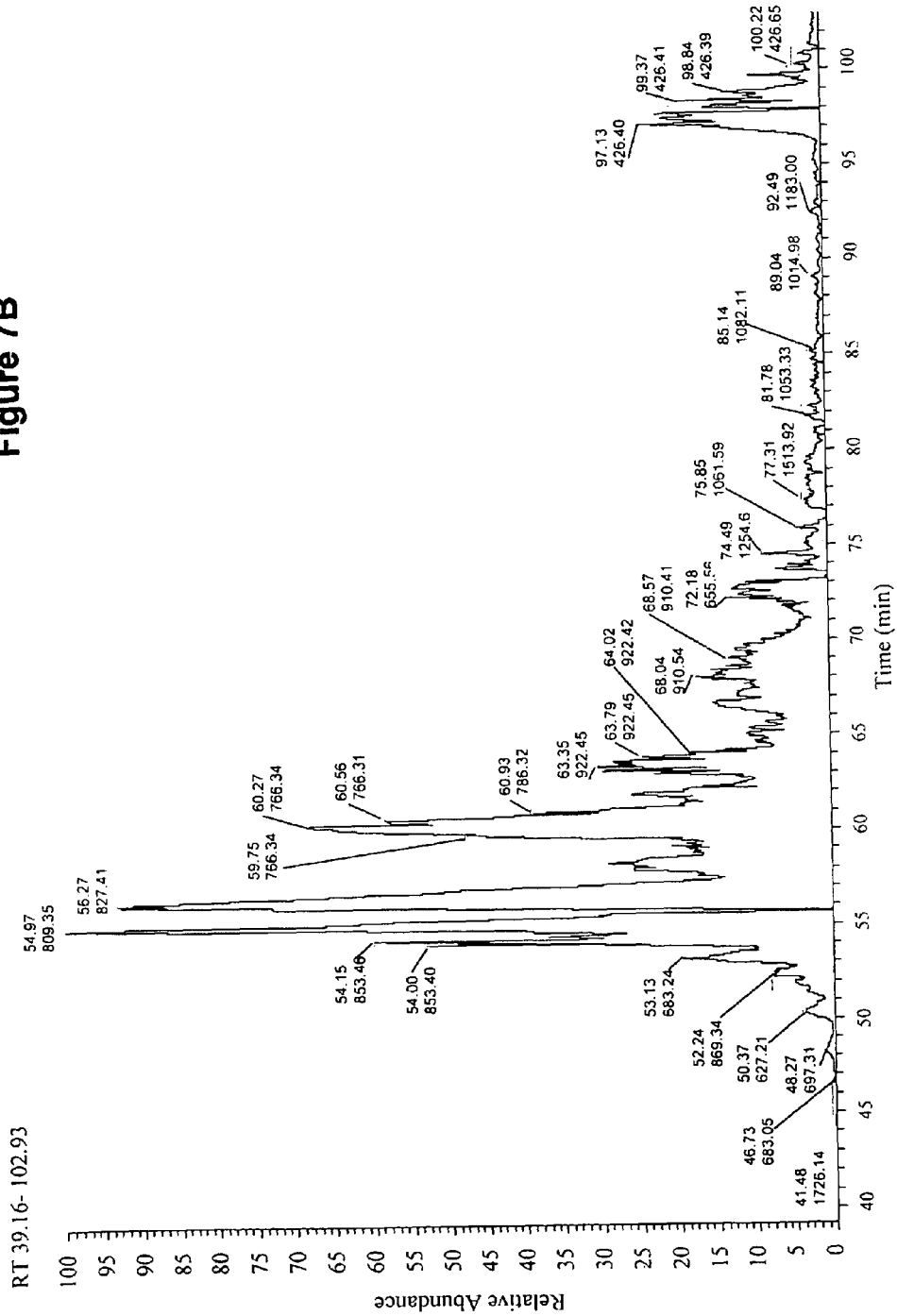

Eluting samples of cultured and aortal (control) elastin analyzed via mass spectrometry generated all the peaks corresponding to peptides of masses equal to predominant peptides present in rat elastin, as listed in a commercial database (Bioworks 3.2 rat database). Representative mass spectroscopy spectra are illustrated in FIG. 7 for peptides derived by elastase digestion of elastin matrices isolated from native rat aortae (FIG. 7A), and smooth muscle cell layers exposed to exogenous HA oligomer supplements (FIG. 7B) and cultured on HA oligomer-tethered substrates (FIG. 7C). Irrespective of source, the spectra contain almost identical peaks, primarily contained within a mass range of 100-922 Da, that reflect similar relative abundance of content of peptides of designated mass or mass/charge ratios contained in the commercial database. A total of n=9 samples/case were analyzed and good repeatability of outcomes was observed.

Example 3

Concomitant delivery of TGF-β or IGF-1 growth factors and HA were studied for effect on elastin synthesis and fiber formation in a cell culture.

Adult rat aortic (RA) SMCs ($5 \times 10^4$ cells/2.4 $cm^2$) were cultured with exogenous HA including oligomers (4-mers, 0.76 kDa), VLMWHA (20 kDa), LMWHA (200 kDa), HMWHA (1.5 MDa), or no HA (control) (n=3/case), with or without TGF-β (1 ng/ml) or IGF-1 (500 ng/ml) according to methods as described above in Example 1. Results are summarized in FIGS. 8-18.

Figures 10, 11:
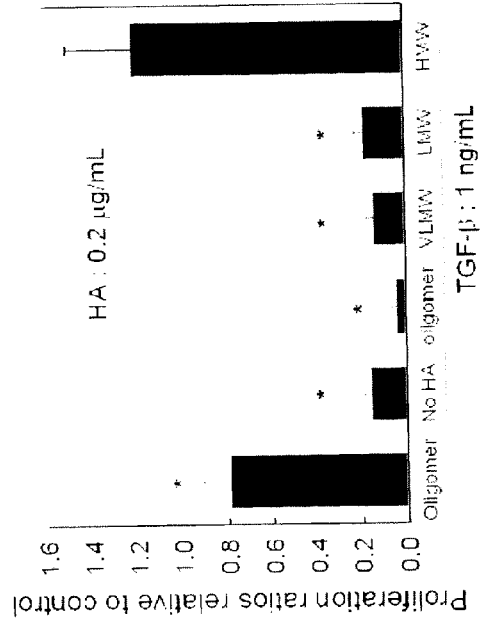
FIG. 10 describes the total matrix elastin, ratios of matrix elastin to the total elastin and ratios of insoluble elastin to total matrix elastin, synthesized by rat aortal smooth muscle cells (RASMCs) supplemented with HA fragments and IGF-1.
FIG. 11 illustrates the effect of HA fragments with TGF-β1 on proliferation of RASMCs.

FIGS. 8-10 summarize treatment-specific trends in proliferation of adult RASMCs as well as in matrix synthesis. With reference to FIG. 8, single and double upward pointing arrows indicate moderate but significant and dramatic (greater than about 5-fold) increases, respectively, an equal sign indicates no significant change, and single and double downward pointing arrows indicate likewise decreases in the biochemical outcomes.

FIG. 11 illustrates the effect of HA fragments and TGF-β1 on RASMCs. Proliferation ratios represent DNA content at 21 days relative to that of a 1 day culture. In all Figures, values shown represent mean±standard deviation of n=3 repeats/case and differences vs. controls were significant (*) for $p < 0.05$.

Figure 12A:
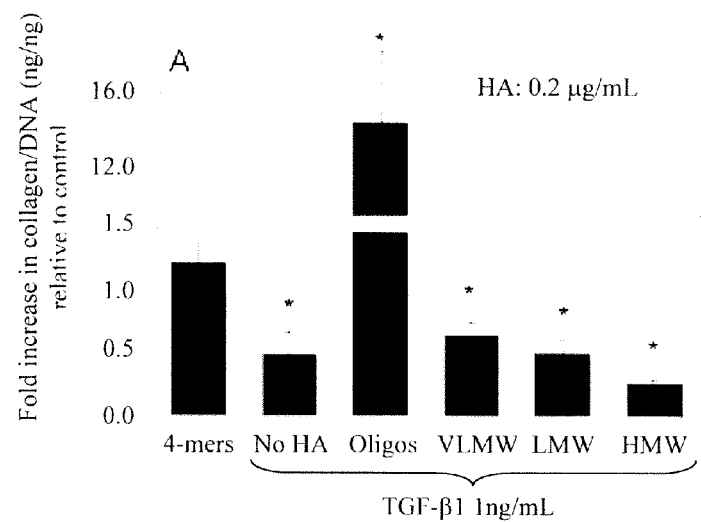
FIGS. 12A and 12B illustrate the impact of HA fragments with TGF-β1 on RASMC collagen matrix synthesis (FIG. 12A) and total collagen output (FIG. 12B)
Figure 12B:
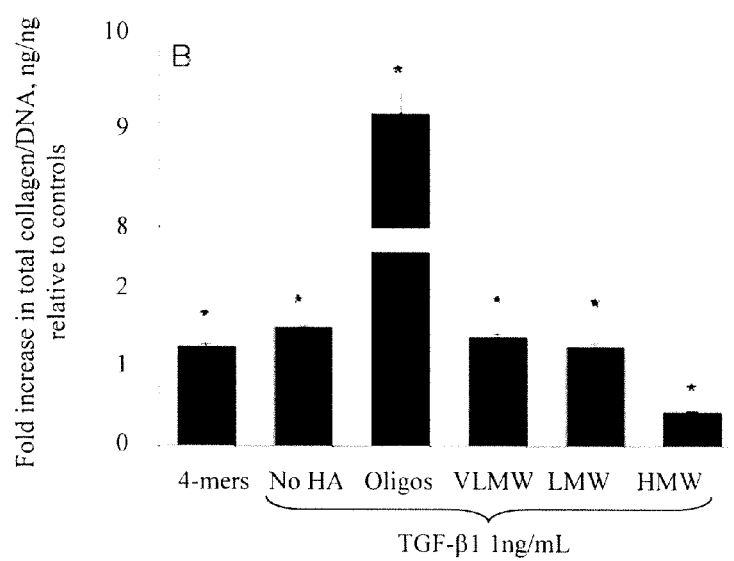

FIGS. 12A and 12B illustrate the impact of HA fragments and TGF-β1 on collagen matrix synthesis (FIG. 12A) and total collagen output (FIG. 12B) including pooled medium and matrix fractions.

Figure 13A:
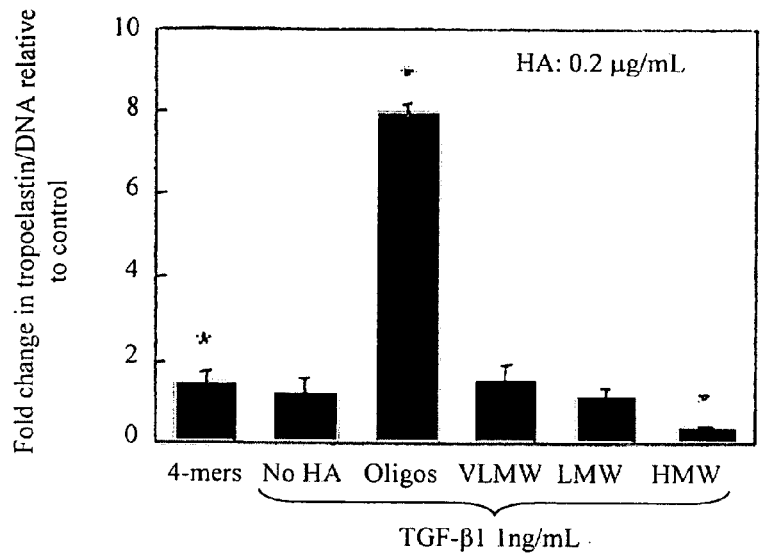
FIGS. 13A-D illustrate the effects of exogenous HA fragments and TGF-β1, alone and together, on synthesis of tropoelastin (FIG. 13A), on alkali-soluble elastin (FIG. 13B), on alkali-insoluble crosslinked elastin (FIG. 13C) and the casewise trends for desmosine and insoluble elastin production (FIG. 13D)
Figure 13B:
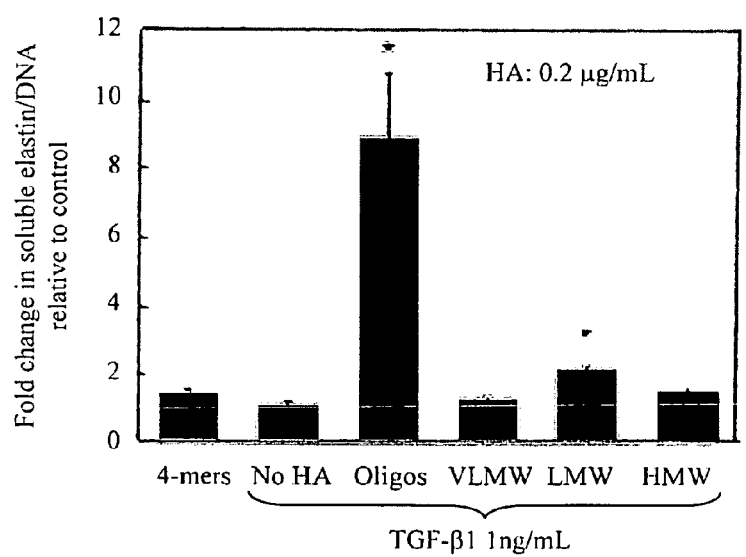
Figure 13C:
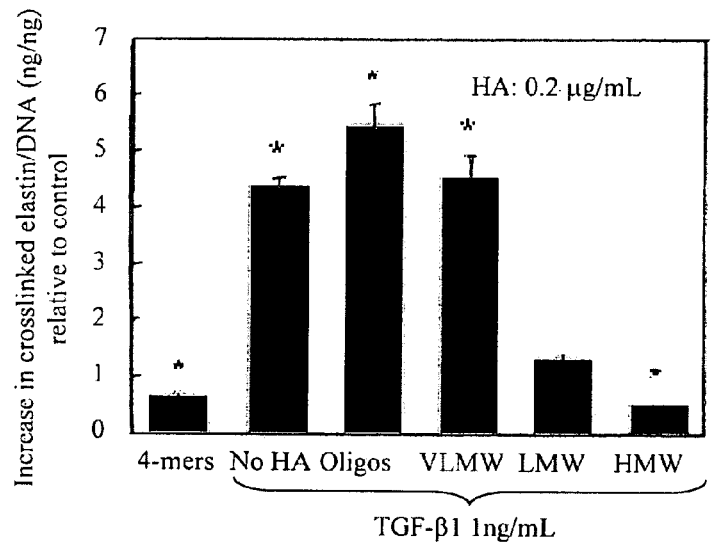
Figure 13D:
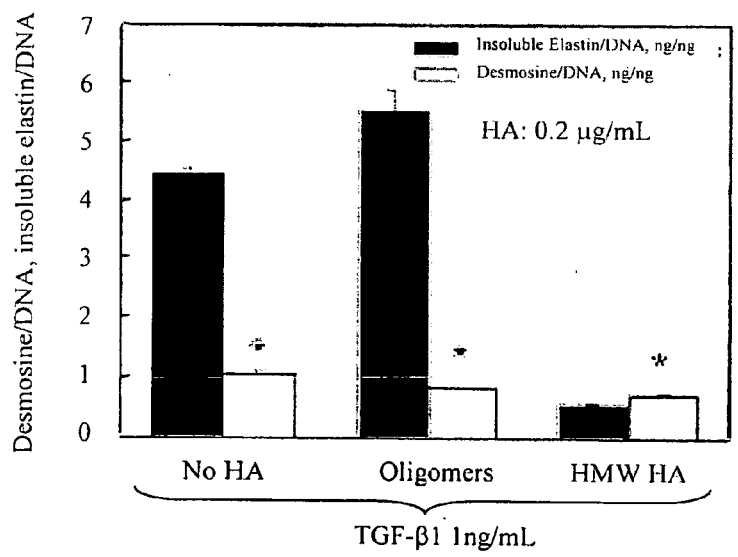

FIGS. 13A-D illustrate the effects of exogenous HA fragments and TGF-β1, alone and together, on synthesis of tropoelastin (FIG. 13A), on alkali-soluble elastin (FIG. 13B) and on alkali-insoluble crosslinked elastin (FIG. 13C). FIG. 13D illustrates that case-wise trends for DNA normalized amounts of desmosine mirrored that of insoluble matrix elastin.

FIGS. 14A and 14B illustrate LOX enzyme activities (FIG. 14A) and LOX protein synthesis (FIG. 14B). Measurements were obtained from test cultures at 16 day culture periods. SDS-PAGE/Western blots showed that TGF-β1, either alone or together with HA fragments enhanced LOX protein synthesis.

Figure 15:
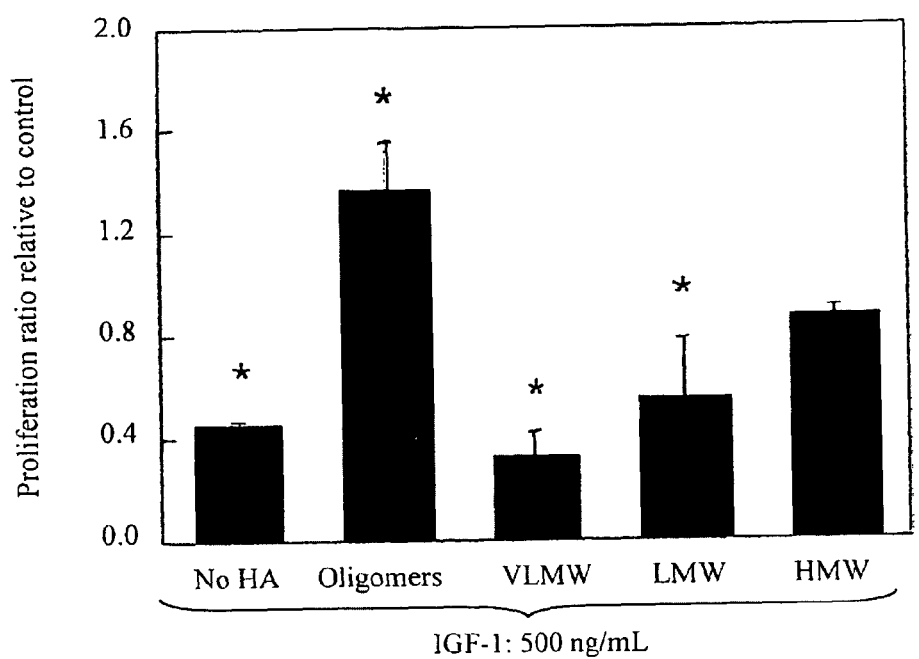
FIG. 15 illustrates proliferation ratios of RASMC cultures supplemented with IGF-1 alone or together with HA fragments.

FIG. 15 illustrates proliferation ratios of RASMC cultures supplemented with IGF-1 (500 ng/mL) alone and together with HA fragments. Data illustrates content of cell layers following 21 days of culture.

Figure 16A:
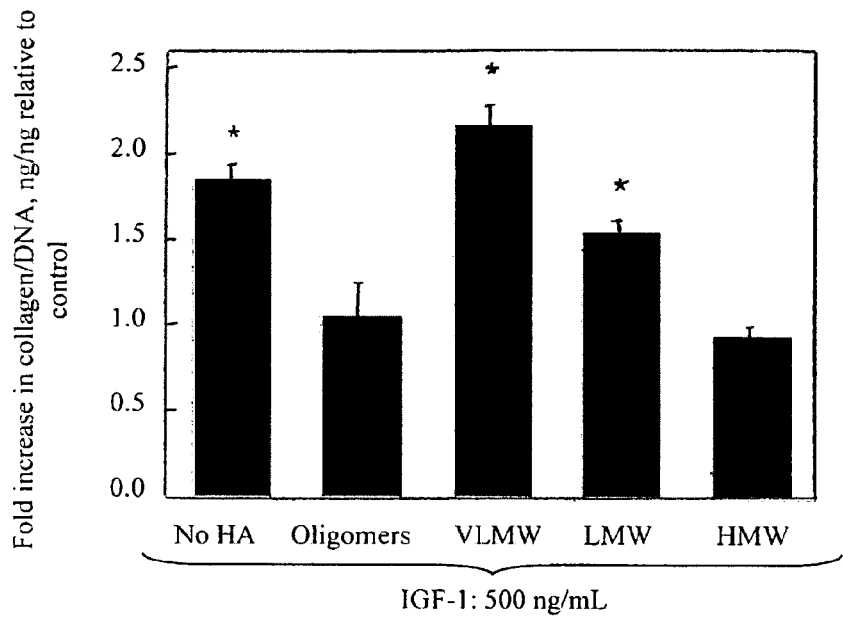
FIGS. 16A and 16B illustrate the effects of IGF-1 with or without HA fragments on matrix collagen (FIG. 16A), and on total collagen (FIG. 16B) synthesis by adult RASMCs.
Figure 16B:
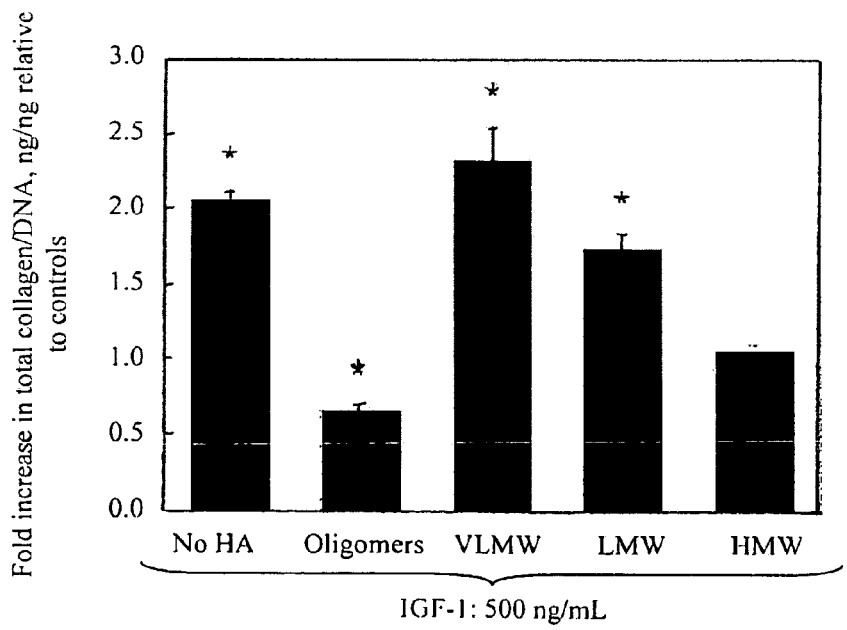

FIGS. 16A and 16B illustrate the effects of IGF-1 (500 ng/mL) with and without HA fragments on synthesis by adult RASMCs of matrix collagen (FIG. 16A), and total collagen (FIG. 16B).

Figure 17A:
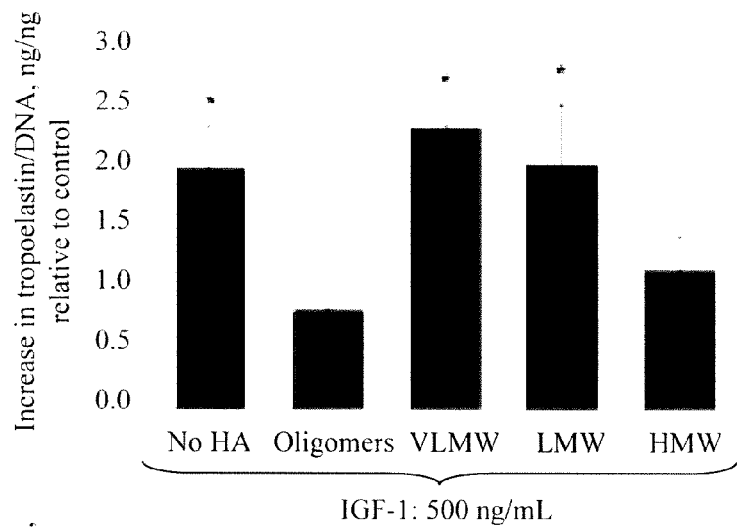
FIG. 17 illustrates elastin production by RASMCs cultured with IGF-1 alone and together with HA fragments including tropoelastin (FIG. 17A), alkali-soluble matrix elastin (FIG. 17B), and alkali-insoluble highly crosslinked matrix elastin (FIG. 17C)
Figure 17B:
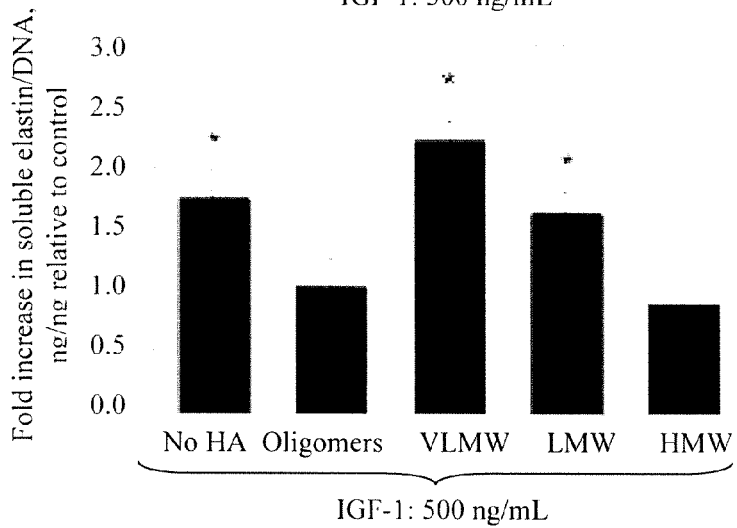
Figure 17C:
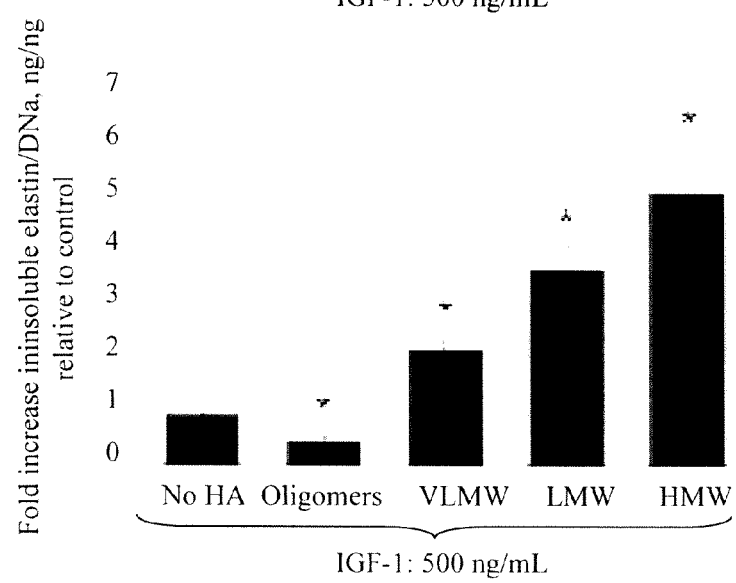

FIG. 17 illustrates elastin production of tropoelastin (FIG. 17A), alkali-soluble matrix elastin (FIG. 17B), and alkali-insoluble highly crosslinked matrix elastin (FIG. 17C) by RASMCs cultured with IGF-1 alone and together with HA fragments.

Figure 18:
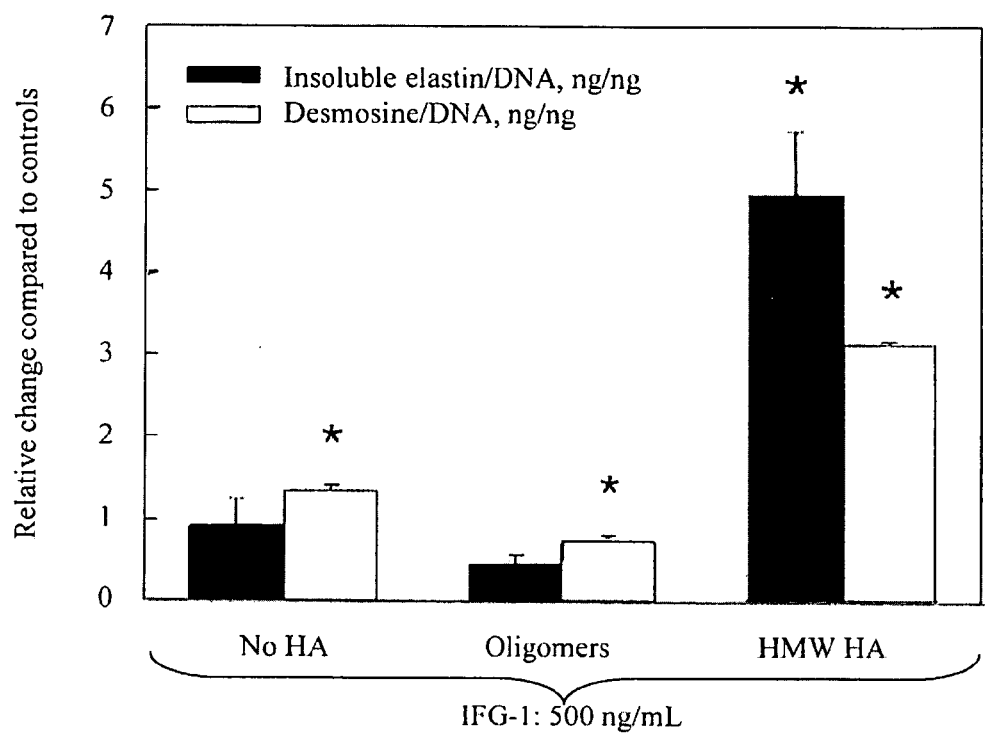
FIG. 18 illustrates desmosine amounts measured in selected test cell layers normalized to corresponding DNA amounts (ng/ng)

FIG. 18 illustrates desmosine amounts measured in selected test cell layers normalized to corresponding DNA amounts (ng/ng). A similar ratio was obtained for the non-HA controls. Comparable trends were observed for the desmosine/DNA density and respective insoluble matrix elastin/DNA for selected cases.

Overall, TGF-β was found to inhibit collagen production in inverse correlation to the added HA fragment size while IGF-1 showed the opposite effect. Collagen synthesis was more down-regulated in the presence of HMW HA relative to the other fragment sizes. In the presence of TGF-β or IGF-1 only, total matrix production at 3 weeks increased by 270±12% and 150±20% respectively. As can be seen in FIGS. 8-18, addition of HMW HA suppressed total elastin matrix production relative to control (TGF-β/IGF-1 only) and shorter HA fragments up-regulated elastin matrix synthesis in inverse correlation to HA fragment size. In addition, TGF-β was found to significantly enhance the crosslinking of soluble tropoelastin into matrix elastin.

Cell proliferation increased 5 fold in 21 days in additive free control cultures; IGF-1 inhibited this by 50% in all the cases except in the presence of oligomers and HMWHA. Collagen production increased 2.1±0.2 fold when VLM-WHA and LMWHA were added in the presence of IGF-1, while HMWHA and HA oligomers had no effect. IGF-1 stimulated tropoelastin production in inverse correlation to the added HA-fragment size, except in the presence of HA oligomers, which suppressed tropoelastin expression by 20±3%. HA fragments upregulated elastin matrix synthesis in inverse correlation to their size. The addition of IGF-1 only with no HA did not upregulate elastin matrix production compared to control. IGF together with oligomers inhibited elastin matrix synthesis by 40±10%. Western blot and desmosine assays semi-quantitatively confirmed the observed biochemical trends. IF studies confirmed an abundant fibrous elastin matrix surrounding cells while TEM confirmed fibrillin-mediated elastin fiber deposition.

Results were confirmed through western blot analysis of tropoelastin, through a desmosine assay to gauge cross-linking within matrix elastin, SEM, and TEM as described above in Example 1, to assess elastin matrix ultra-structure. Peptide/amino acid analysis (not shown) demonstrated remarkable similarities between cultured elastin and native rat aortic elastin.

Example 4

HA with molecular weights of 2000 kDa (HMWHA), 20 kDa (VLMWHA), and 0.76 kDa (oligomers, primarily 4-mers), were dissolved in sterile culture medium prior to addition to cell cultures. The HA oligomer mixtures containing predominantly 4-mers (75±15% w/w, with 6-mers and 8-mers forming the balance) were prepared in the lab using protocols described above. RASMCs were seeded onto 6-well tissue culture plates (Becton Dickinson Labware, N.J.) at a density of $3 \times 10^4$ cells/well and treated with DMEM containing 10% v/v FBE and 1% v/v penstrep. HA/fragments prepared in serum-rich medium was added to cell cultures at an ultimate dose of 0.2 μg/mL. Copper sulfate (Sigma Aldrich, USA) was dissolved in distilled water and supplemented exogenously to the culture wells at finial doses of either 0.1 M or 0.01 M, except in control cultures, which received no supplements. The culture medium was replaced twice weekly, and the spent medium from each well pooled over the 21 day culture period, and frozen for further biochemical analysis. To isolate the observed effects on RASMCs as due to $Cu^{2+}$ and not $SO_4^{2-}$ ions, sodium sulfate ($Na_2SO_4$; Sigma Aldrich; 0.01 and 0.1 M) was supplemented instead of $CuSO_4$ in control cultures.

Figure 19:
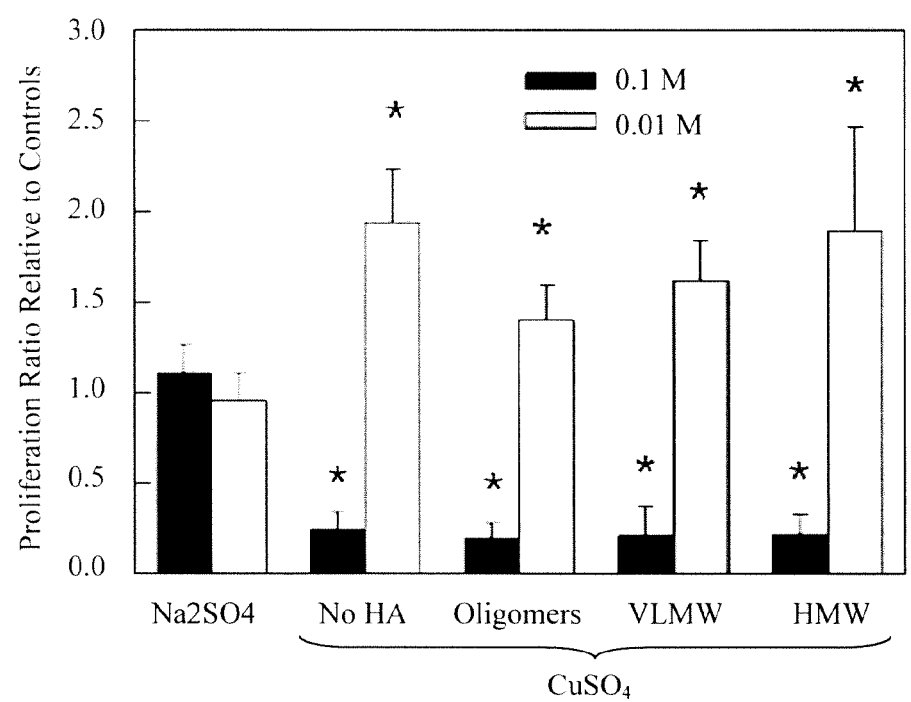
FIG. 19 illustrates proliferation ratios of RASMCs supplemented with sodium sulfate or copper sulfate together with HA fragments.

Proliferation ratios of RASMCs cultured in the presence of either copper sulfate alone or together with HA/fragments/oligomers are shown in FIG. 19. The effects of sodium sulfate addition are also shown for comparison. Addition of sodium sulfate alone had no effect on RASMC proliferation (p=0.4 vs. controls), irrespective of the added dose.

While addition of 0.1 M copper sulfate alone suppressed cell proliferation at 21 days to 0.24+0.1 fold relative to non-additive controls (p=0.005), 0.01 M copper sulfate enhanced the same by 1.9±0.3 fold (p<0.001 vs. control). Independent of provided HA fragment sizes, concurrent delivery of 0.1 M copper sulfate and HA/fragments/oligomers suppressed cell proliferation to 0.2±0.1-fold of control values (p=0.001), while addition of 0.01 M copper sulfate and HA fragments stimulated cell proliferation to extents that appeared to directly correlate to HA size; however differences between intra-group cases were deemed to be statistically insignificant.

Figure 20A:
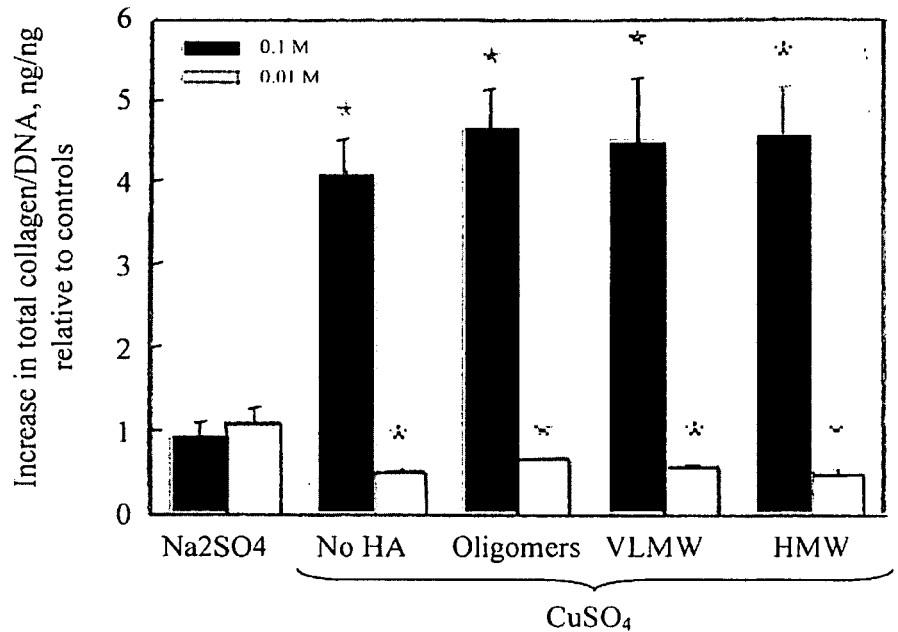
FIGS. 20A-D illustrate the effects of exogenous copper sulfate with or without HA fragments on collagen (FIG. 20A), tropoelastin (FIG. 20B), alkali-soluble matrix elastin (FIG. 20C), and crosslinked alkali-insoluble matrix elastin (FIG. 20D) synthesized by RASMCs.

As shown in FIG. 20A, exogenous supplementation of 0.1 and 0.01 M sodium sulfate did not significantly impact total basal collagen output (matrix+soluble precursors) by RASMCs (0.94±0.15 and 1.1±0.13-fold vs. controls; p=0.2 and 0.1, respectively). When 0.1 M copper sulfate alone was provided, synthesis of collagen (on a per ng DNA basis) increased 4.1±0.4-fold over non-additive controls (1332±140 ng/ng DNA), while addition of 0.01 M copper sulfate suppressed collagen production 0.5±0.04 fold (p<0.001 vs. Controls). In the presence of oligomers, VLMW and HMW HA, 0.1 M copper sulfate enhanced control-levels of collagen synthesis by 4.6±0.4, 4.5±0.8 and 4.5±0.6-fold respectively, while 0.01 M copper sulfate consistently suppressed collagen synthesis in all the cases (p<0.001 vs. controls).

Figure 20B:
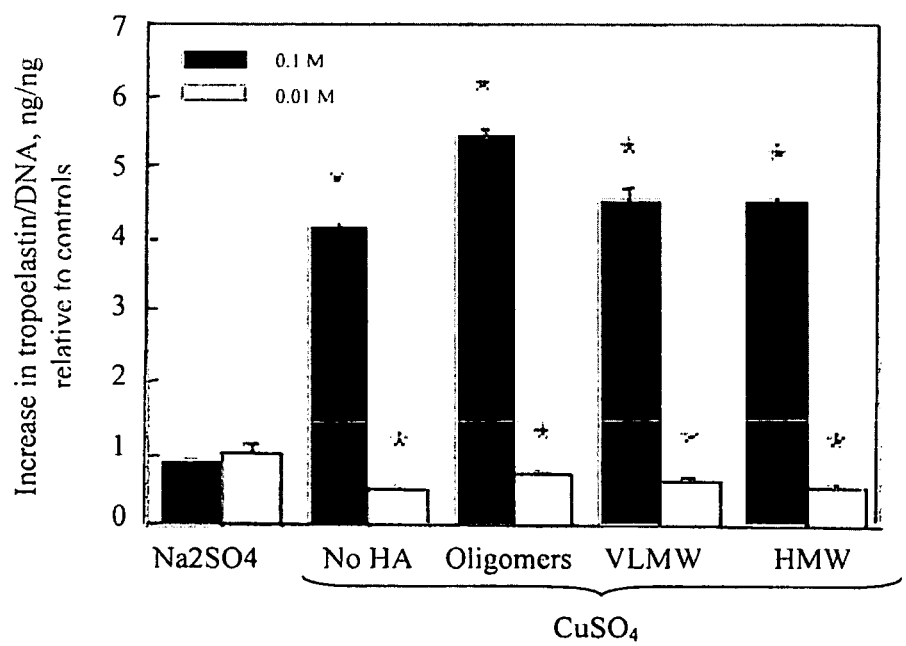

The trends in tropoelastin production by RASMCs (FIG. 20B) closely mirrored those observed for collagen synthesis under identical conditions. Sodium sulfate had no effect on basal levels of tropoelastin production by RASMCs (20074±1240 ng/ng DNA), irrespective of added dose (p=0.5 vs. controls). In the absence of any HA, 0.1 M copper sulfate enhanced control levels of tropoelastin production by 4.1±0.05 fold (p<0.001 vs. control), while 0.01 M copper sulfate inhibited the same by 0.5±0.04-fold (p<0.001 vs. controls). When provided together with HA/fragments/oligomers, 0.1 M copper sulfate likewise enhanced tropoelastin production, while 0.01 M copper sulfate marginally decreased the same (p<0.03 in all the cases vs. controls). No HA fragment size dependent-effects were noted in either case, although in the presence of 0.1 M copper sulfate. HA oligomers stimulated a significantly greater increase in tropoelastin production (1.3 0.01-fold) over cultures that received only copper sulfate (p<0.001).

Figure 20C:
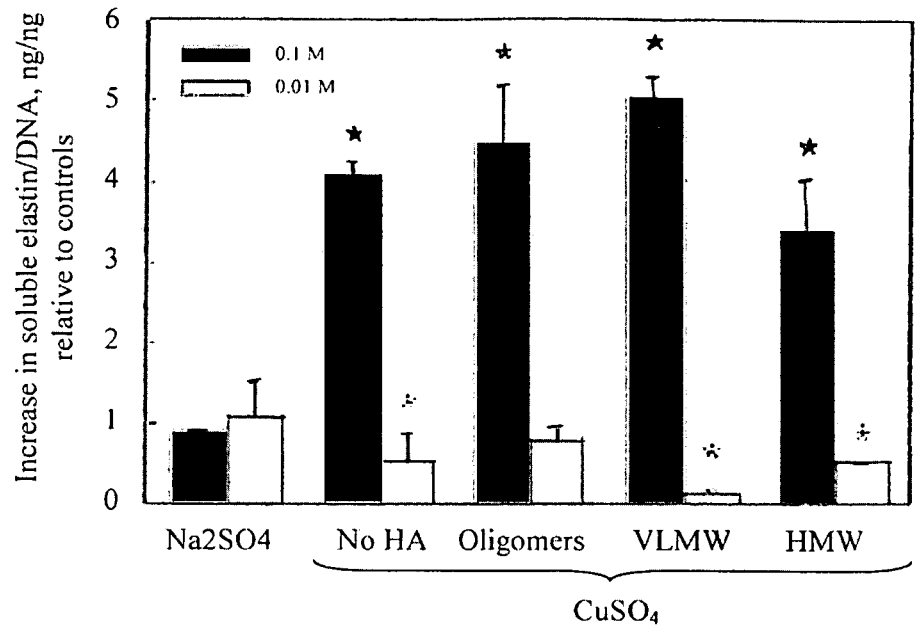

Elastin incorporated into the matrix was measured as a sum of two individual fractions, i.e., a highly cross-linked, alkali-insoluble elastin pellet, and an alkali-soluble fraction. As shown in FIG. 20C, sodium sulfate had no significant effect at either dose (p=0.4 vs. controls). In the absence of HA, addition of 0.1 M copper sulfate increased soluble elastin synthesis dramatically by 4.1±0.1-fold, while 0.01 M copper sulfate inhibited the same by 0.5±0.4 fold, relative to non-additive controls (5388±363 ng/ng DNA; p=0.001 and 0.27 vs. controls, respectively). In the presence of HA/fragments/oligomers. 0.01 M copper sulfate consistently suppressed production of alkali-soluble matrix elastin (p<0.01 vs. controls), while addition of 0.1 M copper sulfate dramatically increased the same by 4.47±0.7, 5.02±0.25 and 3.38±0.6-fold upon concurrent addition of HA oligomers. VLMW. and HMW HA, respectively. Differences in outcomes between these cases were deemed to be statistically insignificant.

Figure 20D:
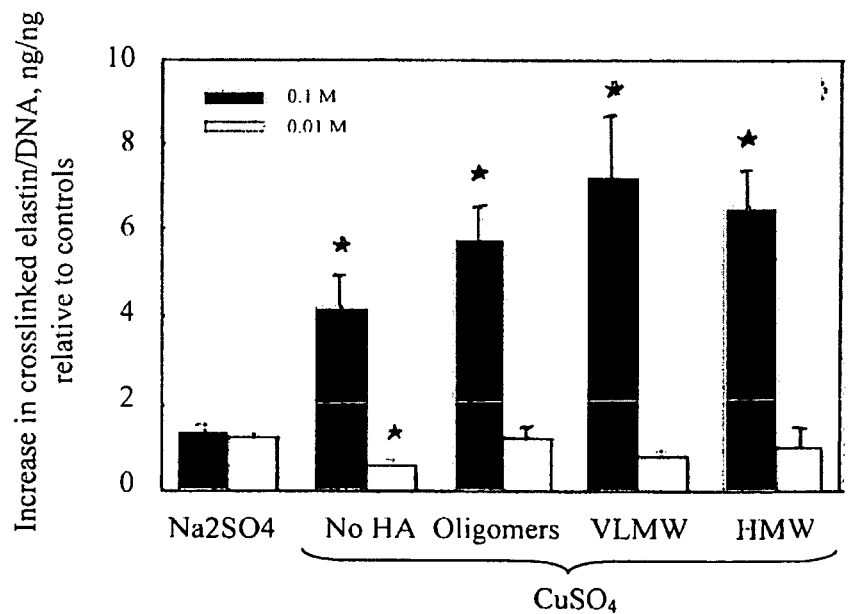

The synthesis of alkali-insoluble, crosslinked matrix elastin (i.e. structural elastin) was not significantly affected by addition of sodium sulfate alone (FIG. 20D). Copper sulfate (0.1 M) alone enhanced control levels of crosslinked matrix elastin synthesis (122+19 ng/ng of DNA) by 4.2 t 0.7-fold, while concurrent addition of oligomers, VLMW and HMW HA increased the same by 5.8±0.7, 7.2±1.4 and 6.5±0.9-fold, respectively (p<0.001 vs. controls in all the cases). However, when 0.01 M copper sulfate was supplemented alone or together with HA fragments, there was no benefit to crosslinked matrix elastin synthesis over controls (0.6±0.1, 1.2±0.2, 0.8±0.1 and 1.02±0.4-fold in the presence of 0.01 M copper sulfate alone or together with oligomers, VLMW and HMW HA, respectively: p>0.05 vs. controls in all the cases).

Figure 21:
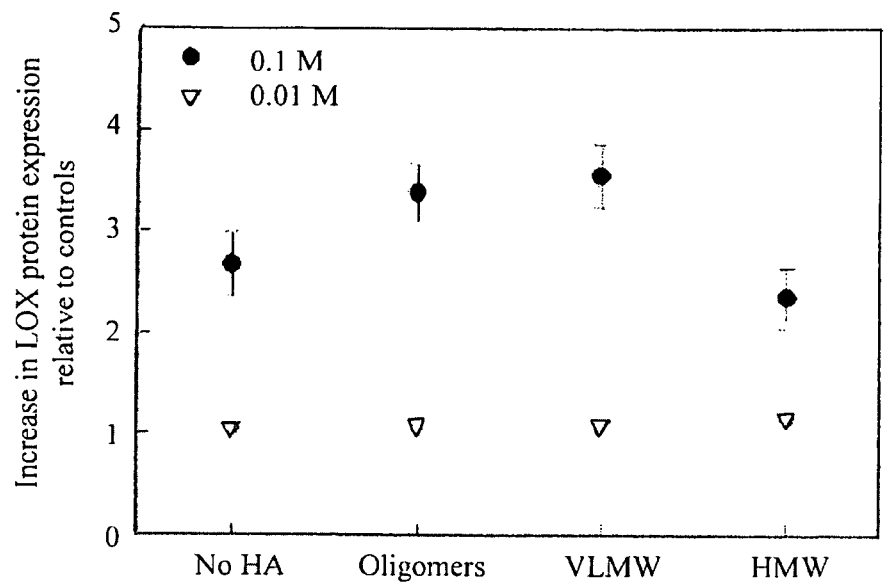
FIG. 21 illustrates LOX protein amounts in polled medium aliquots collected over 21 days of culture for mediums including copper sulfate additive.

DNA-normalized intensities of LOX-protein bands were measured from Western blot analysis in spent medium fractions pooled over 21 days (FIG. 21). Exogenous copper sulfate (0.01 M) both alone and with together with HA fragments did not stimulate LOX protein synthesis compared to controls, and did not show any intra-group differences either. LOX protein synthesis was however enhanced by 2.5-3.5-fold in the presence of 0.1 M copper sulfate alone, and in the presence of HA/fragments/oligomers (p<0.01 vs. controls, in all cases).

Figure 22:
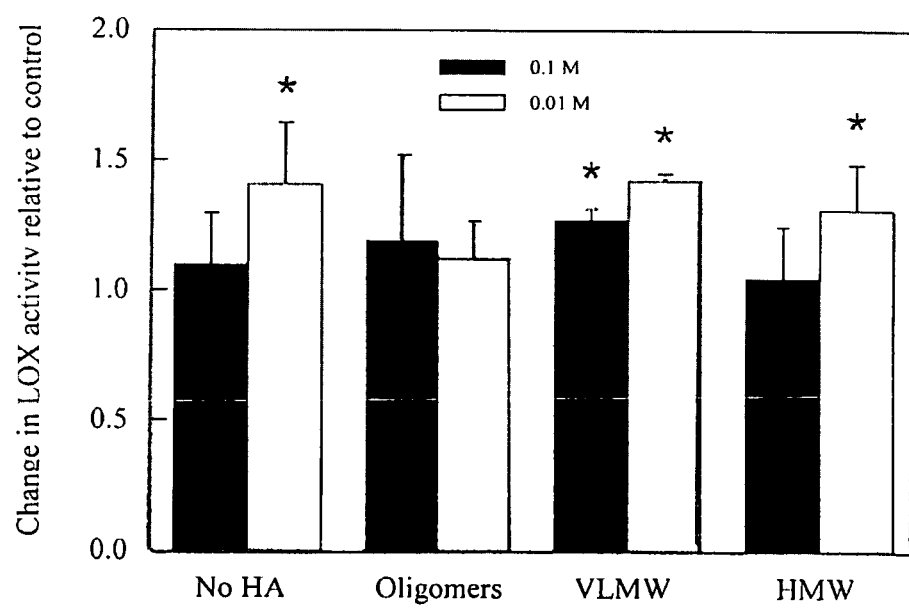
FIG. 22 illustrates LOX enzyme activities in cultures treated with copper sulfate and HA fragments.

The impact of addition of copper sulfates and HA fragments on LOX enzyme activity, measured in spent culture medium following 21 days of culture is shown in FIG. 22. Addition of 0.1 M copper sulfate alone or concurrent with HA fragments had no significant effect on basal LOX functional activity, except in the presence of VLMW HA which stimulated a marginal, but statistically significant increase in LOX activity 1.27±0.04 (p=0.02 vs. controls). LOX activities measured in 0.01 M copper sulfate-supplemented cultures at 21 days were significantly higher than that in controls in most cases (1.4±0.2, 1.12±0.1, 1.4±0.02 and 1.3±0.17 for 0.01 M copper sulfate alone and with oligomers, VLMW and HMW HA, respectively).

Immunofluorescence micrographs of 21-day old cell layers confirmed presence of elastin, fibrillin and LOX (red fluorescence) in cultures that received 0.1 M copper sulfate alone and together with HA fragments. Relative to control cultures, the fluorescence intensity due to elastin were visibly greater in cultures supplemented with copper sulfate, particularly those which also received HA fragments. Fluorescence intensity due to fibrillin was again greater in copper sulfate-supplemented cultures than in controls, though it was most pronounced in cultures that also received VLMW and HMW HA. However, LOX intensity was relatively sparse in all cultures.

Scanning electron micrographs of elastin matrices isolated from 21-day cultures compared to the non-additive control cultures where elastin was sparingly deposited as amorphous clumps, addition of copper sulfate with or without other HA cues appeared to greatly enhance matrix elastin amounts. Addition of 0.01 M copper sulfate alone or together with HMW HA resulted in featureless clump-like deposits, likely of amorphous elastin. Copper sulfate (0.1 M) and HA oligomers together prompted deposition of elongated aggregating elastin fibrils different from the discrete clumps of amorphous elastin that were uniformly distributed within cell layers when 0.1 M copper sulfate was provided alone). When both copper sulfate (0.1 M) and HMW HA were provided together, elastin fiber formation was likewise favored, with the matrix containing greater number of apparently fully-formed fibers than in cultures provided with HA oligomers.

Example 5

RASMCs were cultured as described above at $3 \times 10^4$ cells/well with 0.2 μg/mL HAV oligomers, VLMSHA and HMWHA, as described above. Additives included either copper sulfate ($CuSO_4$, 0.01 M or 0.1 M), sodium sulfate ($Na_2SO_4$, 0.01 M or 0.1 M, 1 μL/mL) as control to alienate effects of $SO_4^{2-}$ ions, or copper nanoparticles (80-100 nm diameter/1 or 10 ng/mL). HA doses were chosen to have insignificant effect on elastin synthesis; growth factor was not added so as to isolate effects of copper ions on LOX; and copper sulfate doses were selected to lie within ranges shown effective with other cell types.

Cells were harvested with 2.5% trypsine0EDTA at 1 and 21 days of culture (0 day used as control) and assayed for DNA, collagen, elastin and LOX production and activity.

Figure 23:
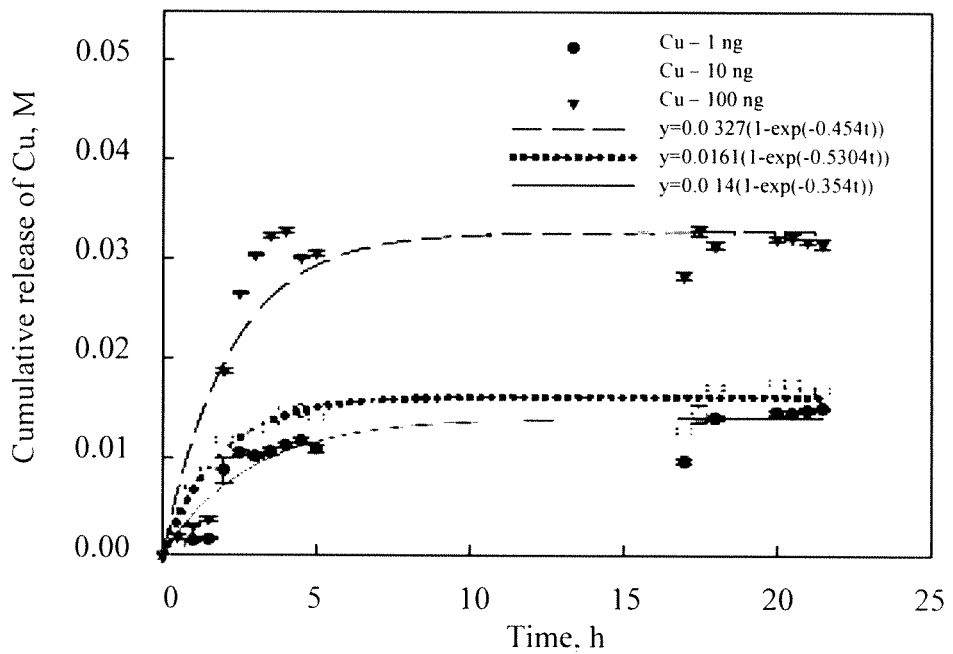
FIG. 23 illustrates cumulative release rates of copper ions from copper nanoparticles in a culture medium.
Figure 24A:
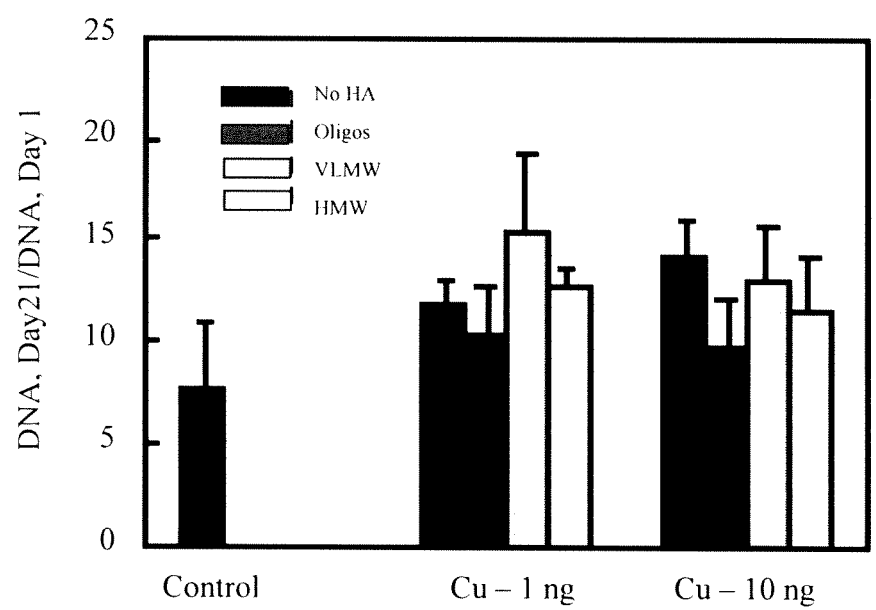
FIG. 24A-E illustrate the effects of copper nanoparticles with or without HA fragments on DNA (FIG. 24A), tropoelastin (FIG. 24B), alkali-soluble matrix elastin (FIG. 24C), and crosslinked alkali-insoluble matrix elastin (FIG. 24D), and total matrix/total elastin (FIG. 24E) synthesized by RASMCs.
Figure 24B:
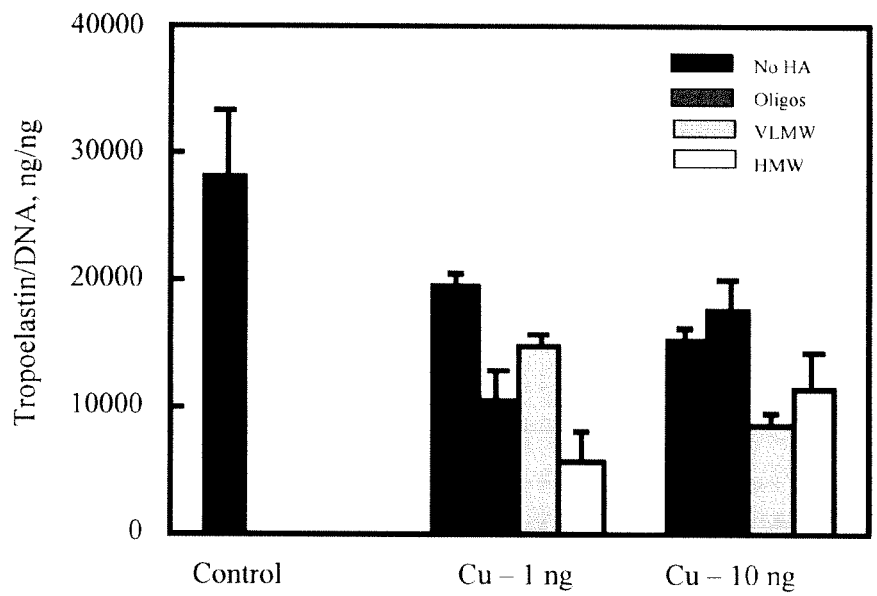
Figure 24C:
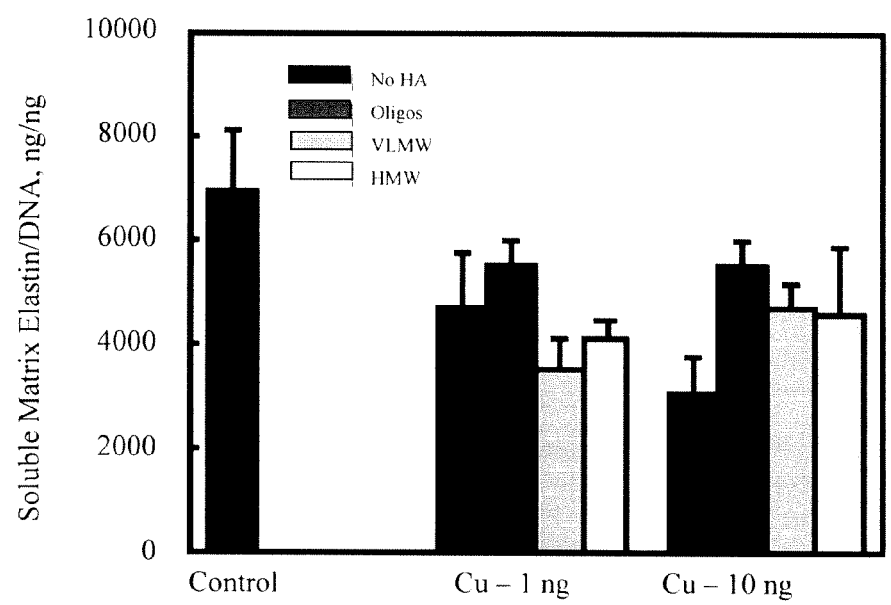
Figure 24D:
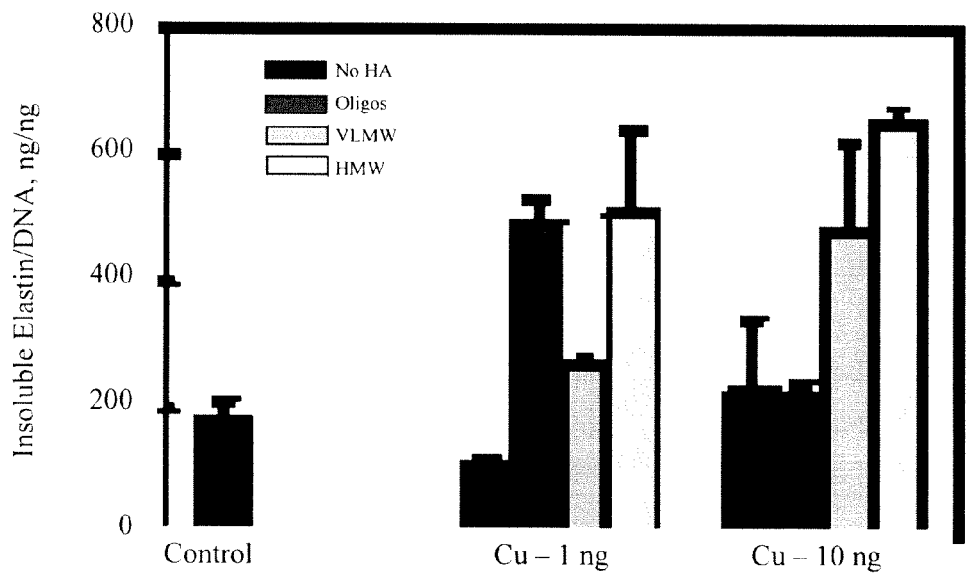
Figure 24E:
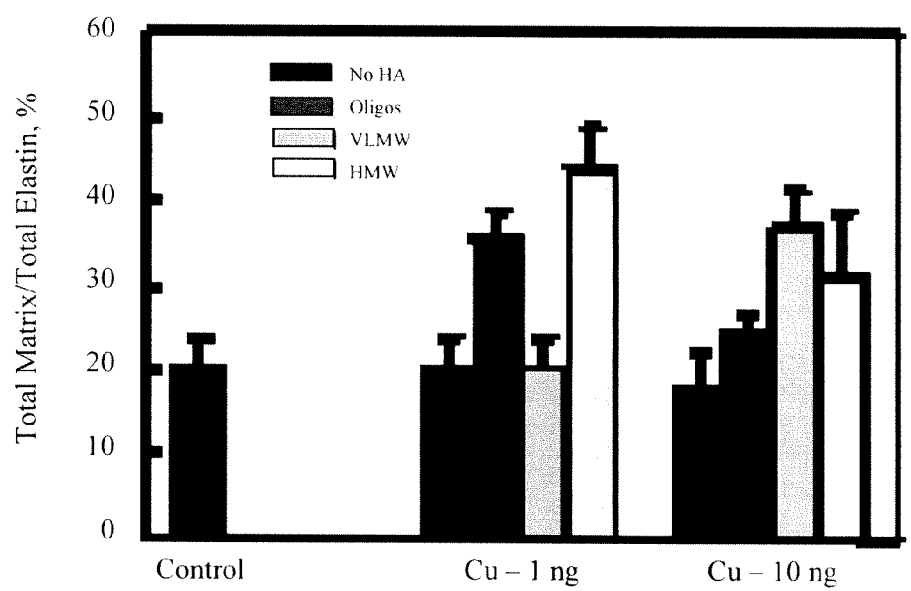

Results are shown in FIGS. 23-25. As can be seen, utilization of copper nanoparticles enabled delivery of copper ions to solution (FIG. 23). In addition, delivery of copper nanoparticles in conjunction with HA can enhance yield and amounts of crosslinked matrix elastin (FIG. 24). FIG. 25 summarizes the effects on LOX production and activity through addition of copper sulfate and copper nanoparticles.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is herein defined and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. An elastogenic composition comprising:
   hyaluronic acid fragments, the hyaluronic acid fragments of the composition having a number average molecular weight of less than about $2 \times 10^6$ Daltons;
   nanoparticles formed of copper, the nanoparticles formed of copper being present in the elastogenic composition at a concentration that delivers copper ions from the nanoparticles in an aqueous environment at a concentration of between about 0.1 μM and about 0.1M; and
   a delivery vehicle for delivering the hyaluronic acid fragments and the nanoparticles formed of copper to a cellular construct including elastin producing cells.

2. The elastogenic composition of claim 1, wherein the hyaluronic acid oligomers of the composition are less than 12 monomer units in length.

3. The elastogenic composition of claim 1, further comprising a growth factor.

4. The elastogenic composition of claim 3, wherein the growth factor is TGF-β.

5. The elastogenic composition of claim 3, wherein the growth factor is IGF-1.

6. The elastogenic composition of claim 1, wherein the delivery vehicle is a tissue engineering scaffold.

7. The elastogenic composition of claim 6, wherein the hyaluronic acid fragments are tethered to the tissue engineering scaffold.

8. The elastogenic composition of claim 1, wherein the delivery vehicle is a sustained release delivery vehicle.

9. The elastogenic composition of claim 1, wherein the nanoparticles are formed of only copper.

10. The elastogenic composition of claim 1, wherein the hyaluronic acid fragments have a molecular weight of between about 0.6 kDa and about 1 kDa.

11. A method for upregulating elastin synthesis by elastin producing cells comprising contacting a cellular construct including elastin producing cells with the elastogenic composition of claim 1.

12. The method according to claim 11, wherein the elastin producing cells are smooth muscle cells.

13. The method according to claim 11, wherein the cellular construct is a natural tissue.

14. The method according to claim 11, wherein the cellular construct is a synthetic cellular construct.

15. An elastogenic composition comprising:
hyaluronic acid fragments, the hyaluronic acid fragments of the composition having a number average molecular weight of between about 0.6 kDa and about 1 kDa; and
nanoparticles formed of copper, the nanoparticles formed of copper being present in the elastogenic composition at a concentration that delivers copper ions from the nanoparticles in an aqueous environment at a concentration of between about 0.1 µM and about 0.1M; wherein the elastogenic composition is a component of a perivascular or endovascular delivery vehicle placeable adjacent a blood vessel wall.

16. The elastogenic composition of claim 15, wherein the perivascular or endovascular delivery vehicle comprises a tubular member.

17. The elastogenic composition of claim 15, wherein the perivascular or endovascular delivery vehicle is a stent.

18. The elastogenic composition of claim 15, wherein the perivascular or endovascular delivery vehicle comprises a sustained-release matrix.

19. The elastogenic composition of claim 15, wherein the perivascular or endovascular delivery vehicle comprises a hydrogel.

20. The elastogenic composition of claim 15, wherein the hyaluronic acid fragments of the composition are less than 12 monomer units in length.

21. The elastogenic composition of claim 15, further comprising a growth factor.

22. The elastogenic composition of claim 21, wherein the growth factor is TGF-$\beta$ or IGF-1.

* * * * *

UNITED STATES PATENT AND TRADEMARK OFFICE
CERTIFICATE OF CORRECTION

PATENT NO. : 8,529,951 B1
APPLICATION NO. : 12/034237
DATED : September 10, 2013
INVENTOR(S) : Anand Ramamurthi et al.

It is certified that error appears in the above-identified patent and that said Letters Patent is hereby corrected as shown below:

Column 1, lines 15 - 19 states,

"The United Stated Government may have rights to the information disclosed herein pursuant to grants from the National Science Foundation (0132573), the National Institutes of Health (EB 0006078-01A1), and the National Center for Research Resources (CO6RR018823)."

Correct this paragraph to read as follows:

-- The United States Government has rights to the information disclosed herein pursuant to Grant No. NSF 0132573, Grant No. NIH EB006078, and Grant No. NIH RR018823 (National Center for Research Resources). --

Signed and Sealed this
Nineteenth Day of January, 2016

Michelle K. Lee
*Director of the United States Patent and Trademark Office*